(12) United States Patent
Akiyama

(10) Patent No.: US 9,155,498 B2
(45) Date of Patent: Oct. 13, 2015

(54) LIVING BODY SENSOR FOR OBTAINING INFORMATION OF A LIVING BODY

(71) Applicant: KABUSHIKI KAISHA TOSHIBA, Minato-ku (JP)

(72) Inventor: Masahiko Akiyama, Tokyo (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 14 days.

(21) Appl. No.: 14/458,913

(22) Filed: Aug. 13, 2014

(65) Prior Publication Data

US 2014/0350366 A1 Nov. 27, 2014

Related U.S. Application Data

(62) Division of application No. 13/487,618, filed on Jun. 4, 2012.

(30) Foreign Application Priority Data

Sep. 26, 2011 (JP) .................................. 2011-209848

(51) Int. Cl.
*H01L 27/00* (2006.01)
*A61B 5/1455* (2006.01)
(Continued)

(52) U.S. Cl.
CPC .............. *A61B 5/1455* (2013.01); *A61B 5/6801* (2013.01); *H01L 27/288* (2013.01); *H01L 27/3244* (2013.01); *H01L 31/167* (2013.01); *H01L 27/3269* (2013.01)

(58) Field of Classification Search
CPC .............. H01L 27/288; H01L 27/3269; H01L 27/3244; H01L 31/167
See application file for complete search history.

(56) References Cited

U.S. PATENT DOCUMENTS

2009/0295769 A1* 12/2009 Yamazaki et al. ............ 345/207
2010/0155578 A1   6/2010 Matsumoto
(Continued)

FOREIGN PATENT DOCUMENTS

CN         101110416 A     1/2008
CN         101122660 A     2/2008
(Continued)

OTHER PUBLICATIONS

Office Action issued Oct. 14, 2013 in Korean Patent Application No. 10-2012-70791 (with English-language translation).
(Continued)

*Primary Examiner* — Caleb Henry
*Assistant Examiner* — Alexander Belousov
(74) *Attorney, Agent, or Firm* — Oblon, McClelland, Maier & Neustadt, L.L.P.

(57) ABSTRACT

According to one embodiment, a photoelectric conversion device including a substrate having opaque interconnection layers, an insulating film formed on the substrate, and having a plurality of openings, light-emitting elements formed of the openings, each light-emitting element having an upper electrode layer, and light-receiving elements formed of the openings, each light-receiving element having an upper electrode layer, wherein a semiconductor material is different in the light-emitting element and the light-receiving element, the upper electrode layer both of the light-emitting element and the light-receiving element are formed as common electrodes, and each interconnection layer is formed on a region outside a region specified by the opening.

7 Claims, 27 Drawing Sheets

(51) Int. Cl.
  *H01L 27/28* (2006.01)
  *A61B 5/00* (2006.01)
  *H01L 31/167* (2006.01)
  *H01L 27/32* (2006.01)

(56) References Cited

U.S. PATENT DOCUMENTS

2011/0024734 A1\* 2/2011 Furst et al. ............ 257/40
2011/0043464 A1  2/2011 Lee et al.

FOREIGN PATENT DOCUMENTS

| JP | 2005-101621 A | 4/2005 |
|---|---|---|
| JP | 2007-81203 A | 3/2007 |
| JP | 2010-153449 | 7/2010 |
| KR | 10-2011-0018755 A | 2/2011 |

OTHER PUBLICATIONS

Office Action issued Oct. 22, 2013 in Japanese Patent Application No. 2011-209848 (with English language translation).

Combined Office Action and Search Report issued Oct. 28, 2014 in Chinese Patent Application No. 201210224418.1 (with English language translation).

\* cited by examiner

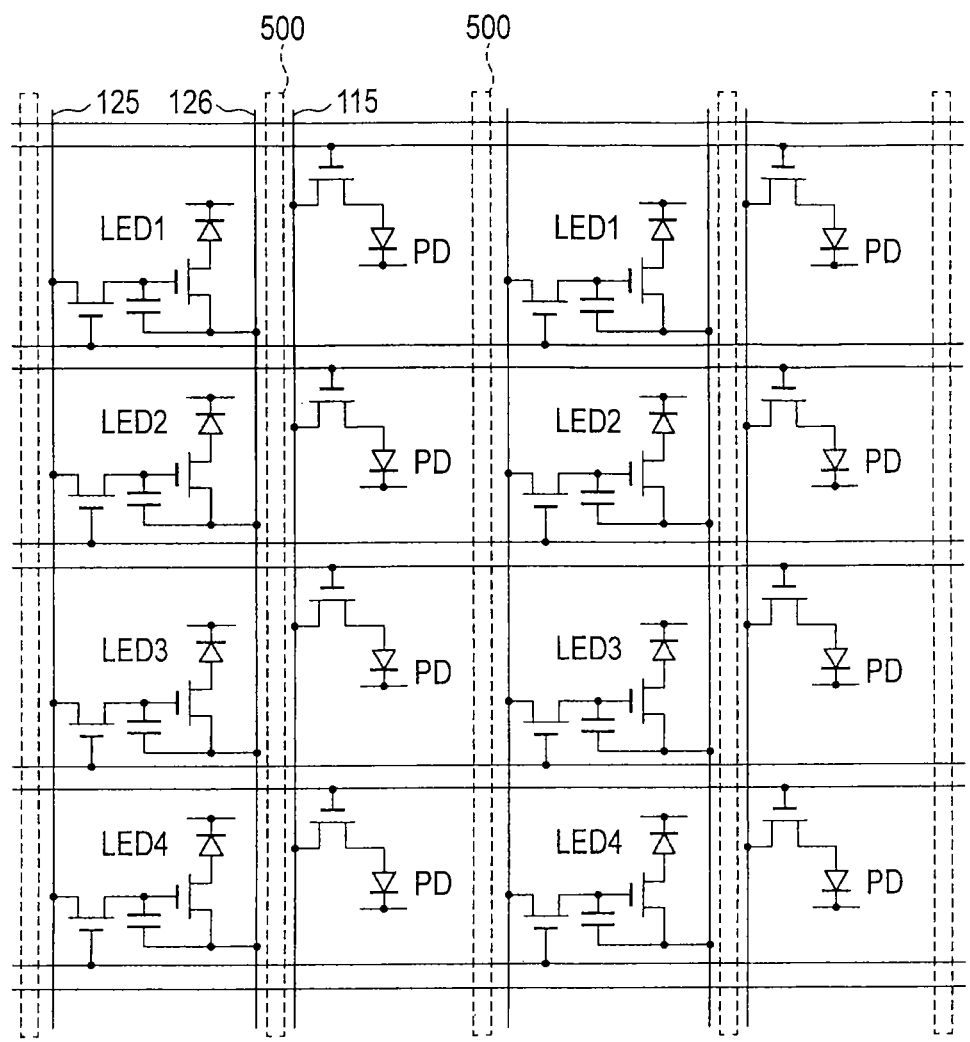
F I G. 8

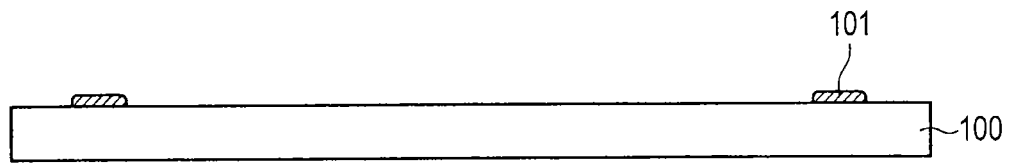
F I G. 9A
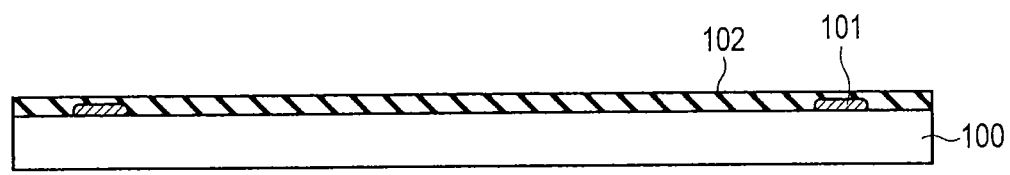
F I G. 9B
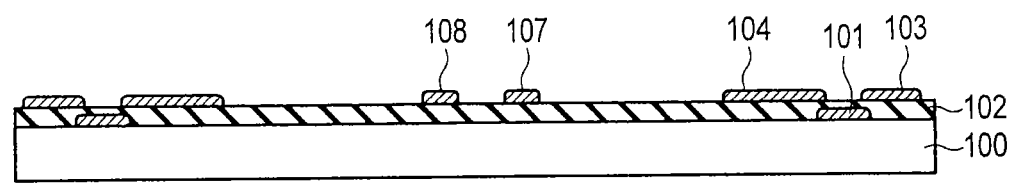
F I G. 9C
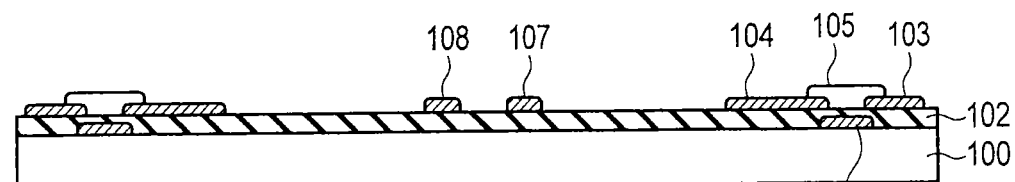
F I G. 9D
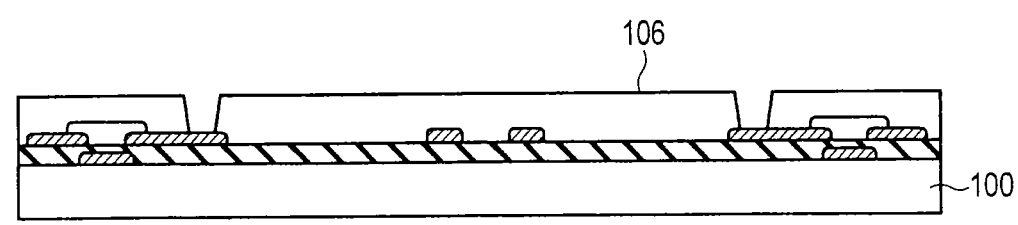
F I G. 9E

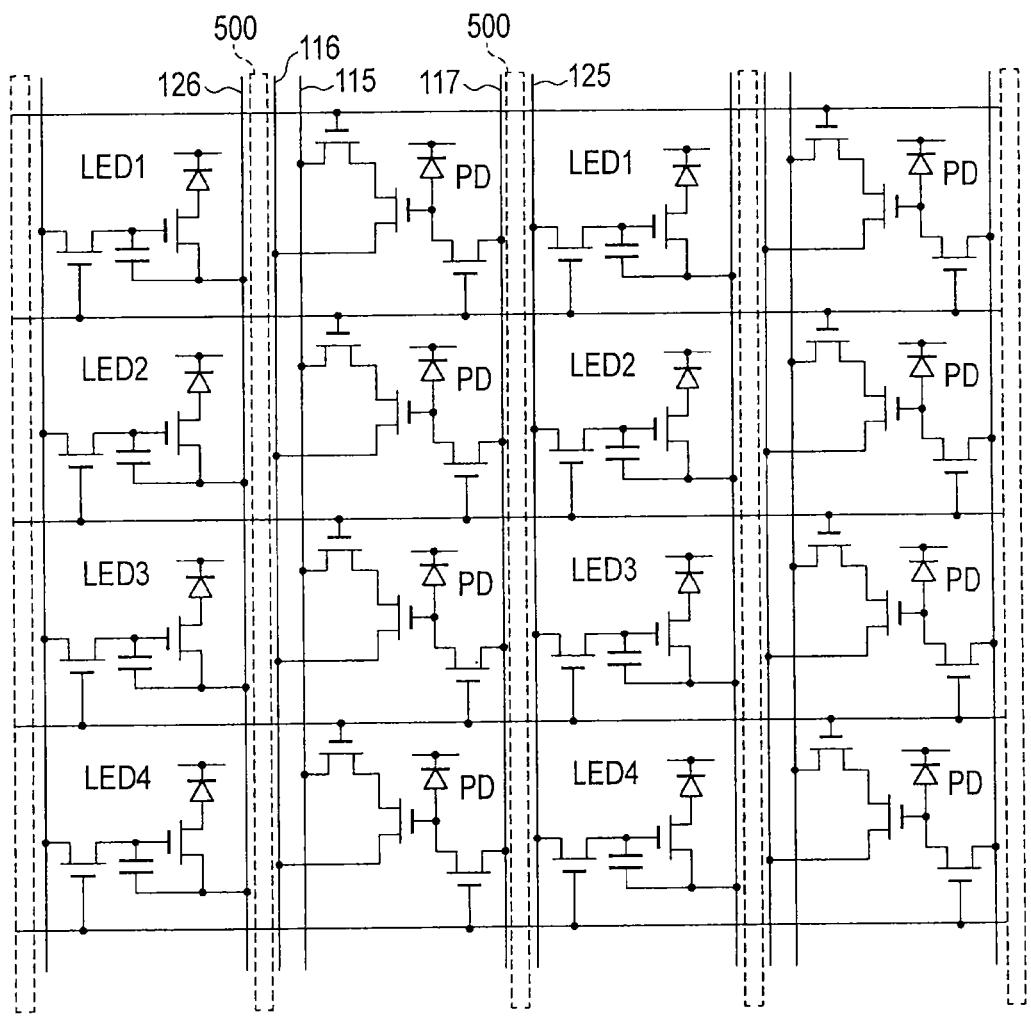
F I G. 12

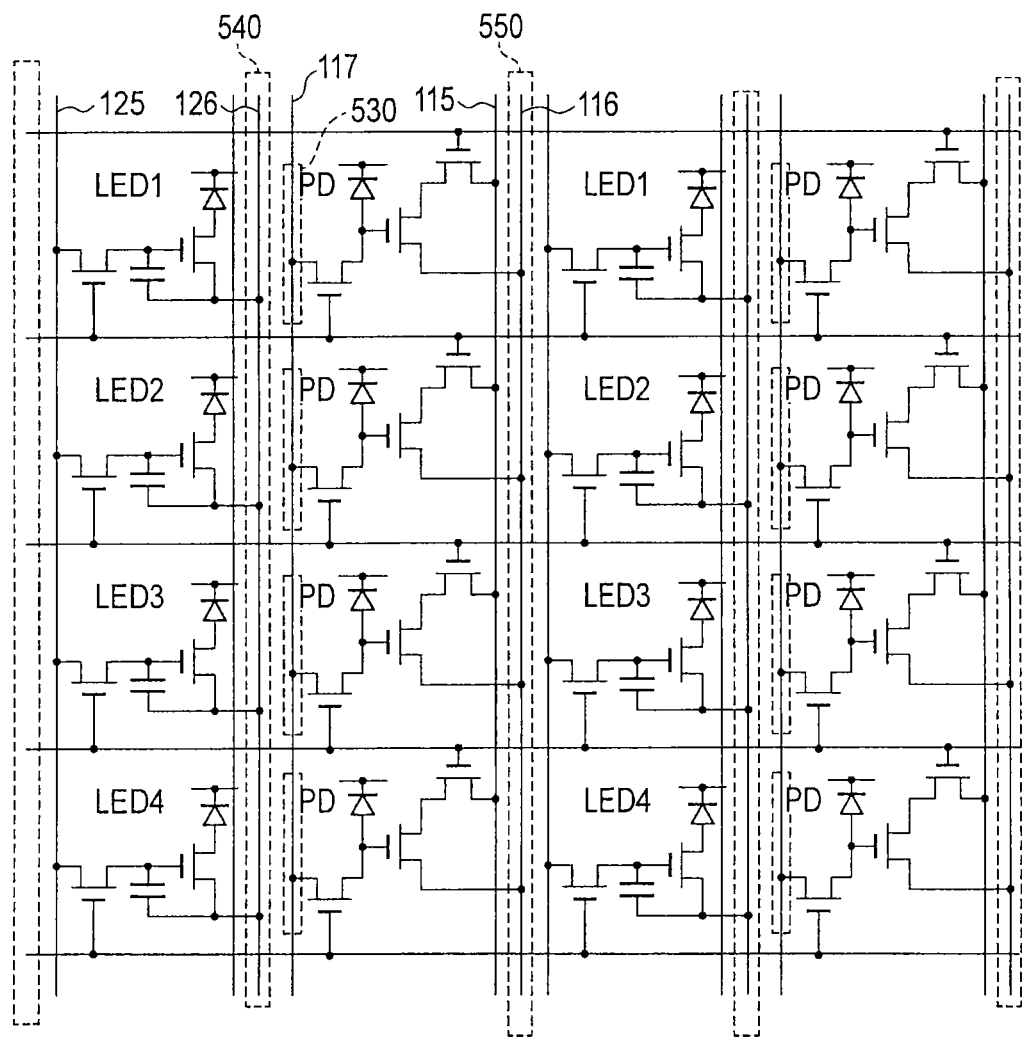
F I G. 19

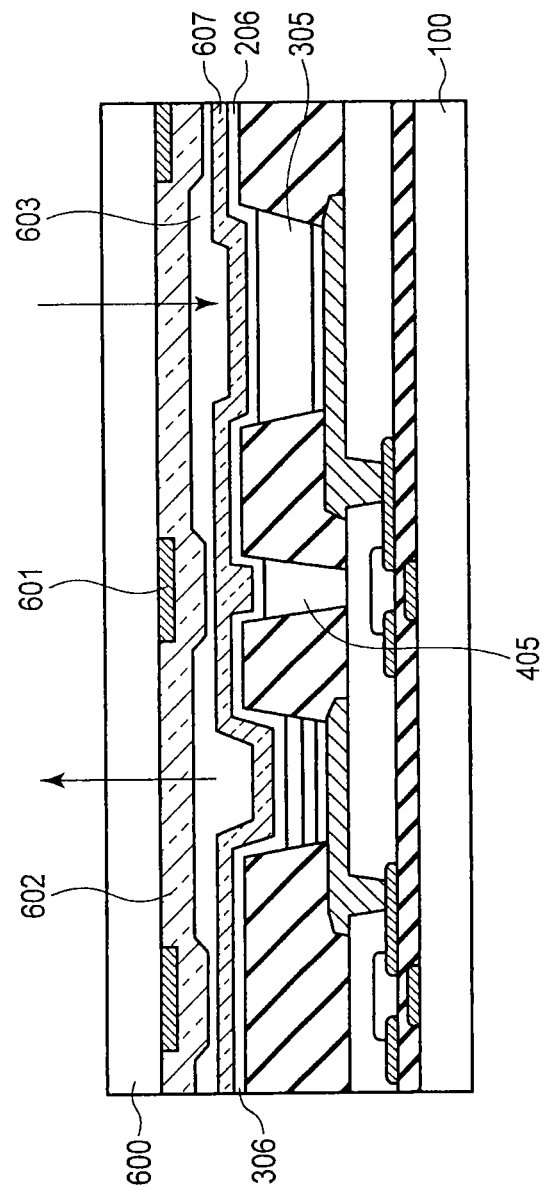
F I G. 23

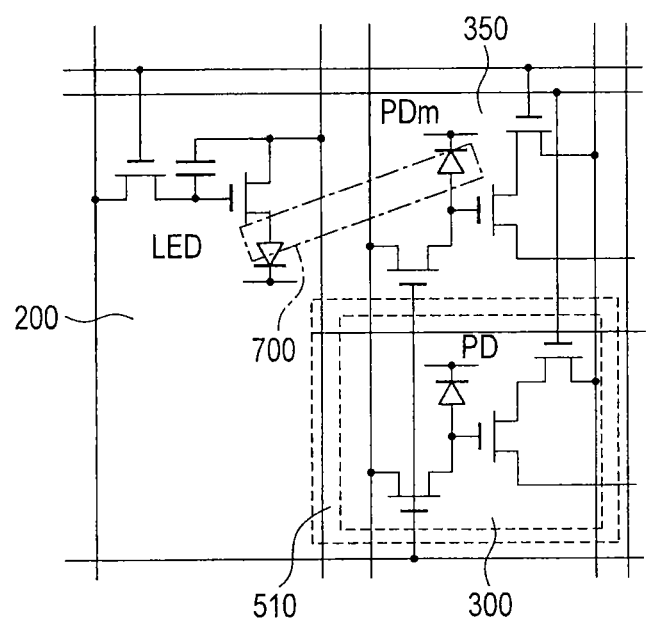
F I G. 26

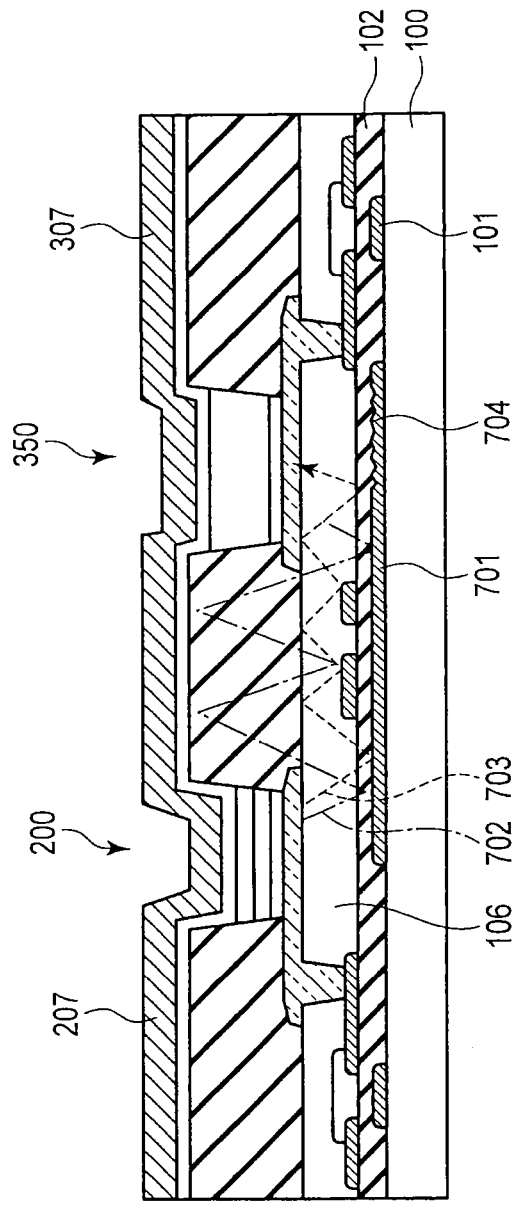
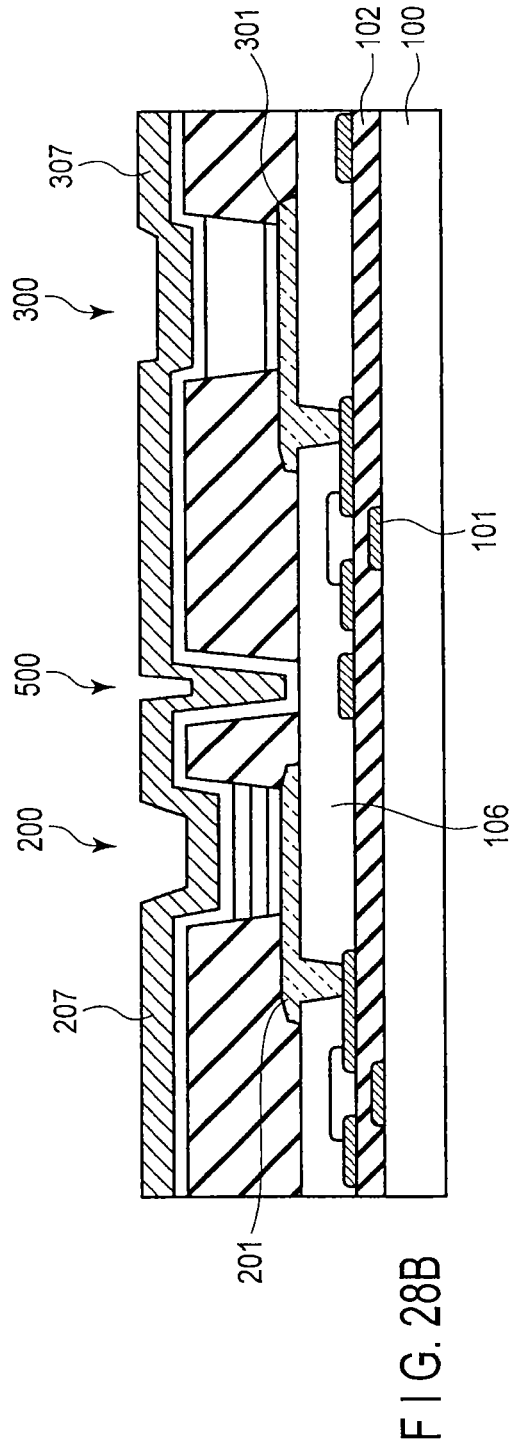
FIG. 28A
FIG. 28B

LIVING BODY SENSOR FOR OBTAINING INFORMATION OF A LIVING BODY

CROSS-REFERENCE TO RELATED APPLICATIONS

This application is a divisional of U.S. application Ser. No. 13/487,618 filed Jun. 4, 2012, and is based upon and claims the benefit of priority from prior Japanese Patent Application No. 2011-209848, filed Sep. 26, 2011, the entire contents of each of which are incorporated herein by reference.

FIELD

Embodiments described herein relate generally to a light source-sensor integrated type photoelectric conversion device and a manufacturing method thereof.

BACKGROUND

In recent years, a light source-sensor integrated type photoelectric conversion device used in a sensor which irradiates a living body with light, and detects its response, a sensor which optically detects a surface state of a display device, and the like has been proposed.

For example, a light source integrated type solid-state imaging device has been proposed as a document reading device of a copying machine. In this solid-state imaging device, a thin-film light-emitting element and a solid-state imaging element (light-receiving element) are independently formed on non-overlapping regions on a substrate. An object is irradiated with light from the light-emitting element, which is extracted on the side opposite to the substrate, and reflected light from the object is detected by the light-receiving element. Since the light-emitting element and light-receiving elements are formed on a single substrate, a state of the object can be accurately detected.

However, in the device of this type, since the light-emitting element and light-receiving element are independently formed on the substrate, their structures are restricted, and much labors are required to manufacture the device. For example, when the light-emitting element is formed after the light-receiving element is formed, an upper layer of the already formed light-receiving element may be damaged upon formation of the light-emitting element, resulting in deterioration of element characteristics. Especially, this problem is conspicuous when organic semiconductor materials are used. Furthermore, when the light-emitting element and light-receiving element are formed on the single substrate, some light rays from the light-emitting element are reflected by respective layers in the device, and enter the light-receiving element, thus causing an increase in detection noise.

As a near-infrared spectroscopy which irradiates a living body with near-infrared light and detects its response to obtain information in the living body, for example, a pulse oximeter has been put into practical use. However, near-infrared light in the living body is easier to be transmitted than visible light, but it is largely scattered. Hence, an amount of reflected light is several percentages or less with respect to incident light. Therefore, detection at a high sensitivity is required. However, in a PIN photodiode of microcrystalline Si, which is popular as a light-receiving element, it is insufficient to obtain a light-receiving element which has a high sensitivity to near-infrared light in terms of a band gap.

BRIEF DESCRIPTION OF THE DRAWINGS

FIG. 8 is a view showing the relationship between pixel units and trenches in a photoelectric conversion device shown in FIG. 6;

FIGS. 9A to 9J are sectional views showing the manufacturing processes of the photoelectric conversion device shown in FIG. 6;

FIG. 12 is a view showing the relationship between pixel units and trenches in a photoelectric conversion device shown in FIG. 10;

FIG. 19 is a view showing yet another example of the relationship between pixel units and trenches in the photoelectric conversion device shown in FIG. 10;

FIG. 23 is a sectional view showing the element structure of a light source-sensor integrated type photoelectric conversion device according to the eighth embodiment;

FIG. 26 is a circuit diagram showing the circuit arrangement of a pixel unit in a light source-sensor integrated type photoelectric conversion device according to the 11th embodiment;

FIGS. 28A and 28B are sectional views showing the element structure in the photoelectric conversion device shown in FIG. 26;

DETAILED DESCRIPTION

In general, according to one embodiment, a photoelectric conversion device comprises: a substrate including opaque interconnection layers; an insulating film formed on the substrate, the insulating film including a plurality of openings which are separated apart in a substrate in-plane direction; light-emitting elements respectively formed in some of the plurality of openings, each light-emitting element including a light-emitting layer formed of a semiconductor material and an upper electrode layer; and light-receiving elements respectively formed in some of remaining openings of the plurality of openings, each light-receiving element including a light-receiving layer formed of a semiconductor material and an upper electrode layer. The semiconductor material of the light-emitting element is different from the semiconductor material of the light-receiving element, and the upper electrode layer of the light-emitting element and the upper electrode layer of the light-receiving element are formed as common electrodes. Furthermore, each interconnection layer is formed on a region outside a region specified by the opening.

A photoelectric conversion device according to embodiments will be described hereinafter with reference to the drawings.

First Embodiment

Figure 1:
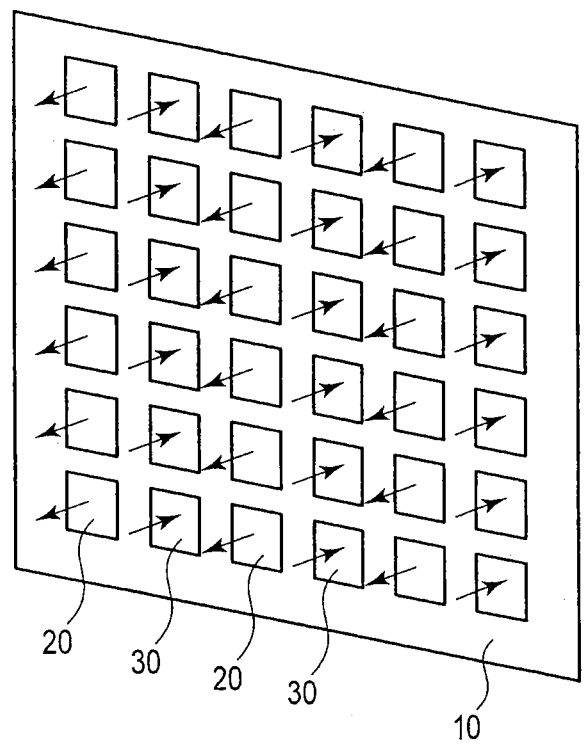
FIG. 1 is a view showing an element layout example of a light source-sensor integrated type photoelectric conversion device according to the first embodiment.

A photoelectric conversion device of this embodiment is configured by laying out light-emitting elements 20 and light-receiving elements 30 on a substrate 10 in a matrix, as shown in FIG. 1. Then, irradiation of light onto an object, and two-dimensional detection of a response of light with which the object is irradiated are attained. Note that in FIG. 1, the light-emitting elements 20 and light-receiving elements 30 are alternately arranged for respective columns. However, this arrangement method allows to set a larger number of light-receiving elements 30 or light-emitting elements 20.

Figure 2:
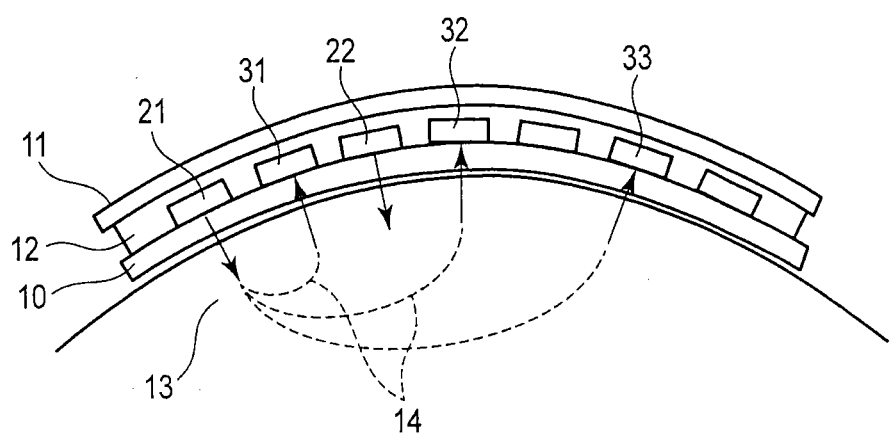
FIG. 2 is a view showing the sectional structure of the photoelectric conversion device shown in FIG. 1.

FIG. 2 shows the sectional structure of the photoelectric conversion device (sensor array) shown in FIG. 1. As shown in FIG. 2, the light-emitting elements and light-receiving elements are alternately laid out on the substrate 10. In FIG. 2, reference numerals 21 and 22 denote light-emitting elements; and 31, 32, and 33, light-receiving elements. To cover the light-emitting elements 21 and 22 and the light-receiving elements 31, 32, and 33, another substrate 11 and a sealing layer 12, which seals between them, are formed. Thus, the elements are protected from an external mechanical force, water, and chemical influences of oxygen, and the like. On the substrate 11, a barrier layer which is hard to transmit gases through it is desirably formed. Also, a material having high barrier properties is desirably selected for the sealing layer 12.

An object 13 is irradiated with light coming from the light-emitting element 21, and its response is detected by the light-receiving elements 31, 32, and 33, thereby detecting information which has been transmitted through and scattered inside the object 13. Since light is received not only by the neighboring pixel (light-receiving element) 31 of the light-emitting element 21 but also by the distant pixels 32 and 33, information which has passed through a deep optical path can be obtained. For this purpose, by adopting an appropriate combination of the positional relationships between the light-emitting elements 20 and light-receiving elements 30, various kinds of information of a living body as well as those in the depth direction can be acquired. Since a signal of the light-receiving element at a distant position becomes weak, the light-receiving element has to be operated to have a high sensitivity, and noise caused by unwanted light has to be prevented.

During another period, in place of the light-emitting element 21, the light-emitting element 22 is controlled to emit light, and that light is received by surrounding light-receiving elements, thus two-dimensionally acquiring information of the object 13. This is particularly effective when the device is applied to a living body sensor. That is, from pieces of information of optical paths 14 through which light rays that enter the respective light-receiving elements pass, the living body sensor can obtain intensities of light rays corresponding to amounts of oxyhemoglobin and deoxyhemoglobin as reflected light rays.

By sequentially emitting light rays of multi-wavelengths (for example, 760 and 840 nm), the amounts of oxyhemoglobin and deoxyhemoglobin can also be spectrally calculated. Also, since a portion such as an arm has a curved surface, it is desirable that the sensor array is flexibly bendable.

Figure 3:
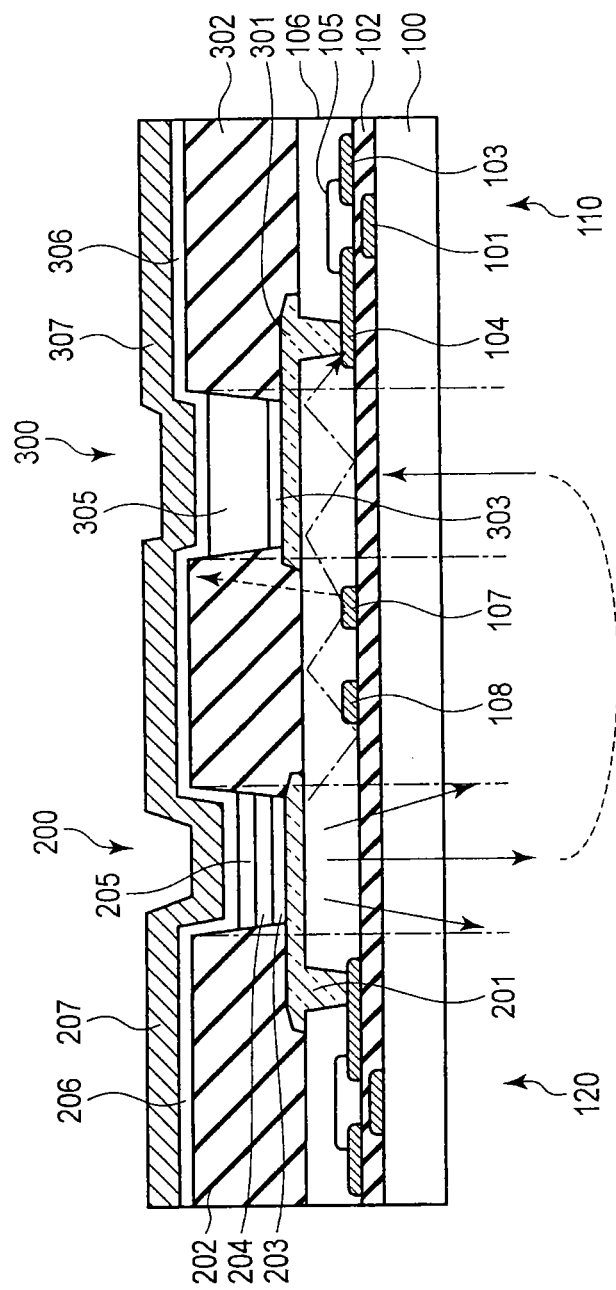
FIG. 3 is a sectional view showing the element structure in the photoelectric conversion device shown in FIG. 1.

FIG. 3 shows the section of the basic structure of this embodiment. An active matrix layer is formed on a transparent substrate 100 which allows light coming from a light-emitting element 200 to transmit through it. That is, driving, control, and reading thin-film transistors (including a thin-film transistor 110 for reading a signal from a light-receiving element 300 and a thin-film transistor 120 for controlling a voltage to the light-emitting element 200), interconnections 107 and 108 (a scan line, signal line, power supply line, and the like), and so forth are formed on the substrate 100.

The transistor 110 on the light-receiving element 300 side is formed of a bottom-gate/bottom-contact organic thin-film transistor configured by a gate 101, gate insulating film 102, source 103, drain 104, and semiconductor layer 105. The transistor 120 on the light-emitting element 200 side has the same configuration as the transistor 110.

An organic semiconductors can be either a low- or high-molecular material, and may be formed by either coating using an ink-jet system or deposition. As a thin-film transistor, not only an organic semiconductor, but also amorphous silicon, microcrystalline silicon, polycrystalline silicon, or a metal oxide such as InGaZnOx may be used as an active layer. Also, various structures such as an inversely staggered type and planar type can be used. Especially, an organic thin-film transistor is preferably applied to a living body sensor because of its high flexibility.

Note that the substrate 100 may be a plastic substrate such as PEN, PES, or PC, or a hybrid substrate made up of glass fibers and an organic resin. Furthermore, the substrate 100 may include a glass substrate as thin as 0.1 mm or less. When an organic resin substrate has permeability to gasses and poses a problem, the substrate formed with a barrier layer may be used. Also, a substrate with electrostatic shield electrodes may be used.

An insulating layer 106, which serves as a passivation layer and interlayer dielectric layer, is formed on the substrate 100 formed with the thin-film transistors 110 and 120. On this insulating layer 106, contact holes required to attain connection to electrodes of the active matrix layer are formed. On the insulating layer 106, transparent electrodes 201 and 301, which are connected to the electrodes of the active matrix layer via the contact holes, are formed. The transparent electrodes 201 and 301 may be formed of ITO, a material prepared by dispersing particulates such as ITO in a resin, or an organic transparent conductive film. On the transparent electrodes 201 and 301 and the insulating layer 106, a bank 202 required to define a region of the light-emitting element 200 and a bank 302 required to define a region of the light-receiving element 300 are formed. The banks 202 and 302 are formed of an insulating film, and are formed with openings in prospective formation regions of the light-emitting element 200 and light-receiving element 300. Bottom portions of the banks 202 and 302 in the openings are located inside the outer circumferences of the transparent electrodes 201 and 301. With this structure, current concentrated portions due to defects or current concentrations caused by edges of pixel electrodes can be prevented from being formed in organic semiconductor layers of a light-emitting layer and light-receiving layer. That is, deterioration of the organic semiconductor layers can be prevented.

The interconnections 107 and 108 of a signal line layer, gate layer, and the like are inhibited from two-dimensionally overlapping upper opening position ranges of the banks 202 and 302. This structure can prevent light rays from the light-emitting layer, which rays have transmitted through the array insulating layer 106, from directly striking the interconnections 107 and 108 and being transmitted toward the light-receiving layer side. In this embodiment, the interconnections 107 and 108 (reflecting electrode layers) are separated from positions immediately below the bank upper openings of the light-emitting layer and light-receiving layer by distances twice or more those corresponding to the thicknesses of the banks. With this structure, even when light rays confined in the insulating layer 106 are scattered, an amount of light that enters the light-receiving layer can be reduced. Also, light rays from the light-emitting layer can be suppressed from being scattered by the interconnections 107 and 108 and being transmitted inside the insulating layer 106. That is, stray light rays inside the substrate, which may disturb reception of very weak light rays, can be suppressed. In this way, the detection sensitivity can be enhanced.

In the light-receiving element 300, a hole injection layer 303 is formed on the transparent electrode 301, and a photoelectric conversion layer (light-receiving layer) 305 is formed on that layer. The photoelectric conversion layer 305 may contain an organic semiconductor. For example, the photoelectric conversion layer 305 may adopt a bulk hetero-structure, which is prepared as follows. That is, after an organic p-type semiconductor and organic n-type semiconductor are dissolved in an appropriate solvent and are coated, the p-type semiconductor and n-type semiconductor are microscopically phase-separated by drying and annealing, so as to form a p-n junction in a self-assembled manner. The hole injection layer 303 can use PEDOT:PSS or NPB. Note that as the layer configuration of the light-receiving element 300, a charge transport layer, an intermediate layer which prevents mutual diffusion between layers, a blocking layer required to confine electric charges, and the like may be included.

On the other hand, the light-emitting layer 200 is formed by stacking a hole injection layer 203, hole transport layer 204, and light-emitting layer 205 in turn on the transparent electrode 201. The light-emitting layer 205 is preferably formed of an organic semiconductor for the purpose of variously changing light-emitting wavelengths. Note that in the light-emitting element 200 as well, an intermediate layer and blocking layer may be formed or the light-emitting layer may adopt a multilayered structure, so as to facilitate electron-hole coupling and confinement of electric charges. The respective layers which configure the light-emitting element 200 and light-receiving element 300 need not always be formed inside the banks but may be formed on the banks. For formation by means of deposition, film formation regions may be specified using a metal mask or the like, so as to provide boundaries on the banks.

Then, an electron injection layer 206 and cathode electrode 207 of the light-emitting element 200, and an electron injection layer 306 and cathode electrode 307 of the light-receiving element 300 are commonly formed. As the electron injection layers 206 and 306, a fluoride such as LiF or CsF or a calcium compound such as Ca can be used. As the cathode electrodes 207 and 307, a metal layer of Al, Ag, or the like can be used.

Since it is desirable for the electron injection layers 206 and 306 to reduce a work function (about 3 eV), the aforementioned material having susceptibility to oxygen and water may be used. By forming the common electron injection layers 206 and 306 and the common cathode electrodes 207 and 307 of the light-emitting element 200 and light-receiving element 300, the light-emitting element 200 and light-receiving element 300 can be formed at the same time even using low resistant materials. For this reason, the characteristics of the light-receiving element 300 and light-emitting element 200 can be improved. Especially, since the light-receiving active layer adopts a bulk hetero-junction, the surface after formation of the light-receiving active layer can be stable. For this reason, even when the respective layers of the light-emitting element 200 are formed after formation of the light-receiving element 300, its influence can be eliminated.

Furthermore, since the cathode electrodes 207 and 307 as common electrodes can be formed on the entire surface, an overall resistance can be reduced. Thus, a voltage drop due to a current in the light-emitting element 200 can be reduced, and electrical coupling between the light-receiving element 300 and another element can be reduced. For this reason, crosstalk can be reduced. In order to protect the electron injection layers 206 and 306 with a low environmental resistance, a sealing layer and sealing substrate (not shown) may be formed immediately after the electrodes are formed. In this case, both the light-emitting element 200 and light-receiving element 300 can maintain high performances without deteriorating their element characteristics.

Emission and reception of near-infrared light require a predetermined band gap, that is, a transition level gap. For this purpose, organic semiconductors having many variations of material characteristics are preferably used for the respective elements. Especially, in element formation on the flexible substrate with a low thermal resistance, organic semiconductors are effectively used to attain low-temperature processes. In addition, since high-performance organic semiconductors can be used, a higher sensitivity and higher performance can be attained.

Figure 4:
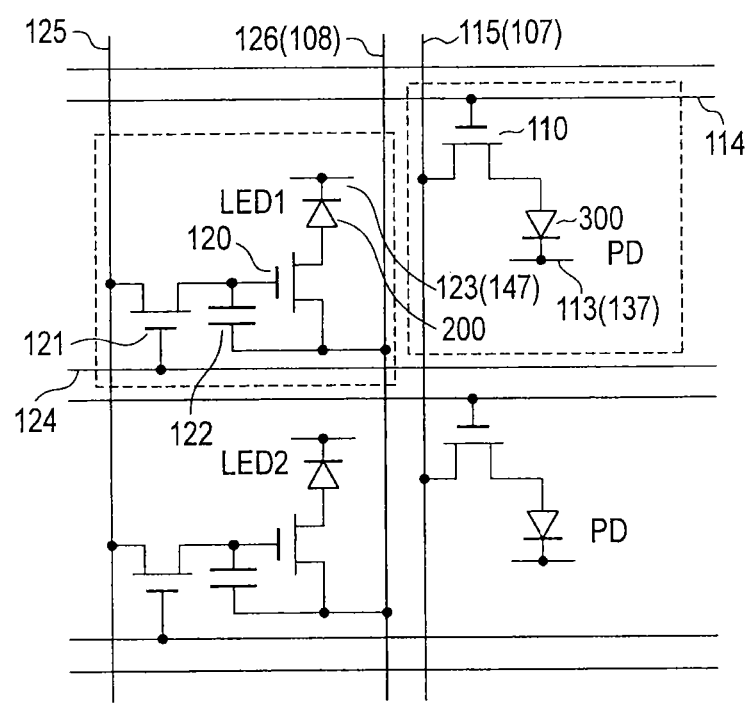
FIG. 4 is a circuit diagram showing the circuit arrangement of a pixel unit in the photoelectric conversion device shown in FIG. 1.

FIG. 4 is a circuit diagram of one pixel unit of this embodiment. The anode of the light-receiving element 300 is connected to a sensor signal line 115 via the transistor 110. The gate of the transistor 110 is connected to a sensor scan line 114. The anode of the light-emitting element 200 is connected to the drain of the driving transistor 120, the source of which is connected to a power supply line 126. To the gate of the driving transistor 120, a storage capacitor 122 and the drain of a control transistor 121 are connected. The other terminal of the storage capacitor 122 is connected to the power supply line 126. The source of the control transistor 121 is connected to a light-emitting element signal line 125, and the gate of the control transistor 121 is connected to a light-emitting element scan line 124. The cathode of the light-emitting element 200 is connected to a cathode electrode 123 (207 in FIG. 3), and that of the light-receiving element 300 is connected to a cathode electrode 113 (307 in FIG. 3). These cathode electrodes 113 and 123 are formed to roughly cover the entire pixel region as common electrodes.

In this circuit arrangement, on the light-emitting element 200 side, the scan line 124 is set at high level (a low voltage as a voltage when the transistor is a p-channel transistor) to enable the control transistor 121, thereby setting a gate voltage of the driving transistor 120 by a signal voltage of the signal line 125. When the scan line 124 goes to low level (a high voltage as a voltage in case of the p-channel transistor) to disable the control transistor 121, a voltage is held by the storage capacitor 122 and a gate capacitance. Then, a current according to that voltage is supplied from the driving transistor 120 to the light-emitting element 200, thus causing the light-emitting element 200 to emit light with a predetermined intensity.

On the other hand, on the light-receiving element 300 side, the scan line 114 goes to high level to enable the transistor 110, thereby causing electric charges of the light-receiving element 300 to flow into the signal line 115. An integration circuit (not shown) is connected to the signal line 115, thereby obtaining an output voltage proportional to the flowed electric charge amount. At the same time, the potential of the signal line 115 is set to be a predetermined value, thereby setting the potential on the anode side of the light-receiving element 300 to be an appropriate bias potential as a detection sensitivity. When the scan line 114 goes to low level to disable the transistor 110, the anode potential of the light-receiving element 300 varies depending on a photocurrent based on the light amount that enters the light-receiving element 300 and the element capacitance. Then, the light-receiving element 300 accumulates electric charges according to a light irradiation amount for a time period until the transistor 110 is enabled next. By sequentially reading these electric charges, a reflection amount of light from an object to be inspected can be detected. Since the light-receiving elements 300 are arranged in a matrix, two-dimensional detection is allowed. Therefore, the light-receiving elements 300 can be used as the sensor shown in FIG. 2 above.

Figure 5:
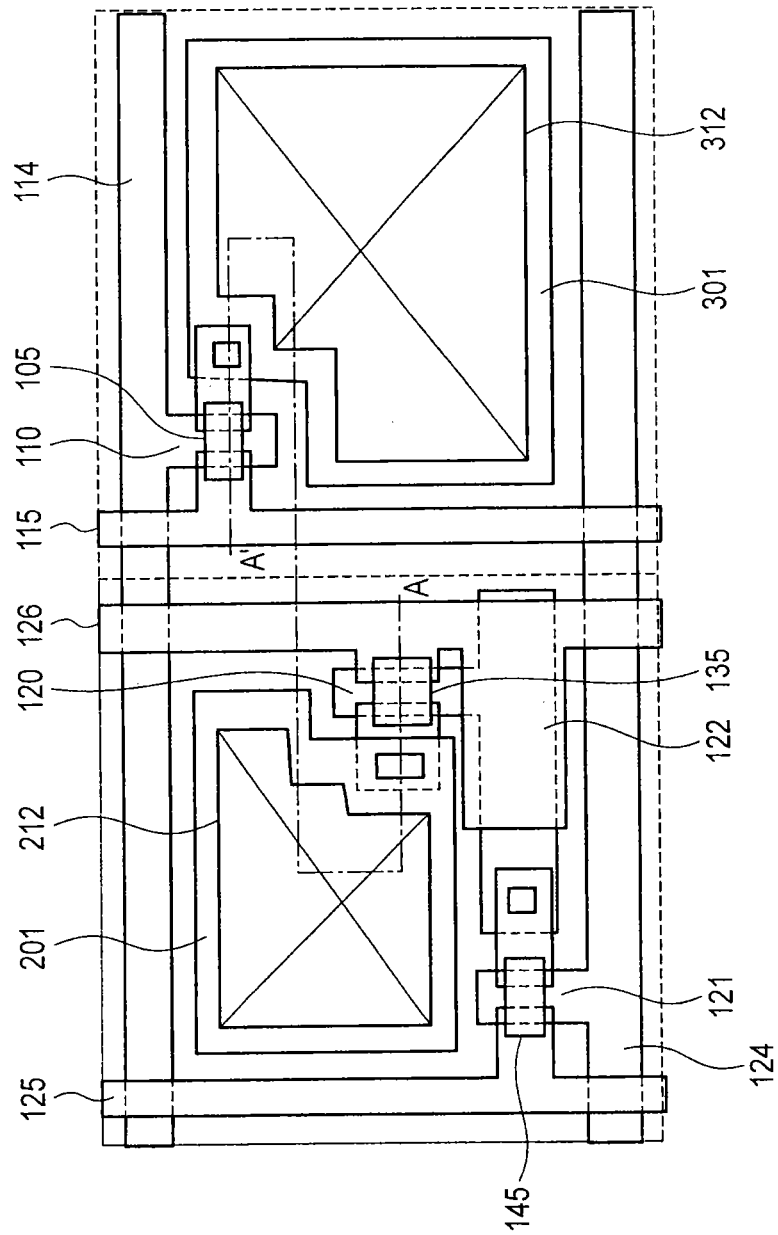
FIG. 5 is a view showing a planar layout of elements corresponding to the element structure shown in FIG. 3 and the circuit arrangement shown in FIG. 4.

FIG. 5 shows a layout of elements corresponding to the section shown in FIG. 3 and the circuit shown in FIG. 4. A section A-A' in FIG. 5 corresponds to FIG. 3. FIG. 5 illustrates elements up to the bank structure, and the light-emitting element, light-receiving element, common electrodes, and the like are not shown.

A bank boundary 312 is formed inside the transparent electrode 301 of the light-receiving element 300, and a region inside this boundary serves as a light-receiving region. To the light-receiving element scan line 114, the gate of the transistor 110 is connected. To the light-receiving element signal line 115, the source of the transistor 110 is connected. To the lower electrode 301 of the light-receiving element 300, the drain of the transistor 110 is connected. The semiconductor layer 105 is formed by coating or deposition of an organic semiconductor.

A bank boundary 212 is formed inside the transparent electrode 201 of the light-emitting element 200, and a region inside this boundary serves as a light-emitting region. The driving transistor 120 and control transistor 121 are formed to have the same configuration as the light-receiving element transistor 110. The storage capacitor 122 forms a lower electrode in the same layer as the gate of the transistor 120 and the scan line 124, forms an insulating layer in the same layer as the gate insulating film 102, and forms an upper electrode in the same layer as the source/drain of the transistor 120 and the signal line 126. The storage capacitor 122 is connected to the transistor 121 via a contact hole. Semiconductor layers 135 and 145 of the transistors 120 and 121 are also formed in the same manner as the semiconductor layer 105 of the transistor 110.

The common layers of the light-emitting element 200 and light-receiving element 300 are formed on the entire surface. However, since these layers are isolated by the banks and passivation/interlayer dielectric layers, no problem is posed in terms of their functions. Furthermore, the cathode electrodes 207 and 307 as common layers serve as shields against external electrostatic noise. For this reason, the light-receiving element 300 can detect even small electric charges without being influenced by noise.

As described above, according to this embodiment, the light-emitting element 200 and light-receiving element 300 are formed on the single substrate 100, the light-emitting layer of the light-emitting element 200 and the light-receiving layer of the light-receiving element 300 use different semiconductor materials, and the charge injection layer 206 and cathode electrode 207 of the light-emitting element 200 and the charge injection layer 306 and cathode electrode 307 of the light-receiving element 300 are commonly formed. With this structure, when an object is irradiated with light and its response is detected, the detection sensitivity can be improved, and noise can be reduced.

More specifically, the light-receiving element 300 with predetermined characteristics (having, for example, a sensitivity to near-infrared light) and the light-emitting element 200 with predetermined characteristics (emitting, for example, a specific wavelength of near-infrared light), which are configured by organic semiconductors, are integrally formed. Then, since their charge injection layers 206 and 306 can use a fluoride or calcium compound which has low resistances (water resistance, chemical resistance, oxidation resistance, and the like) but has a high performance, the high performance can be assured. The common upper electrodes 207 and 307 are formed to be either thick or thin, and do not undergo any annealing. For this reason, the high performance can be assured. Then, since light in an array from the light-emitting element 200 formed on the single substrate 100 can be suppressed from transmitting through the insulating layer and entering the light-receiving element 300, noise can be reduced, and high-sensitivity detection is guaranteed.

Second Embodiment

Figure 6:
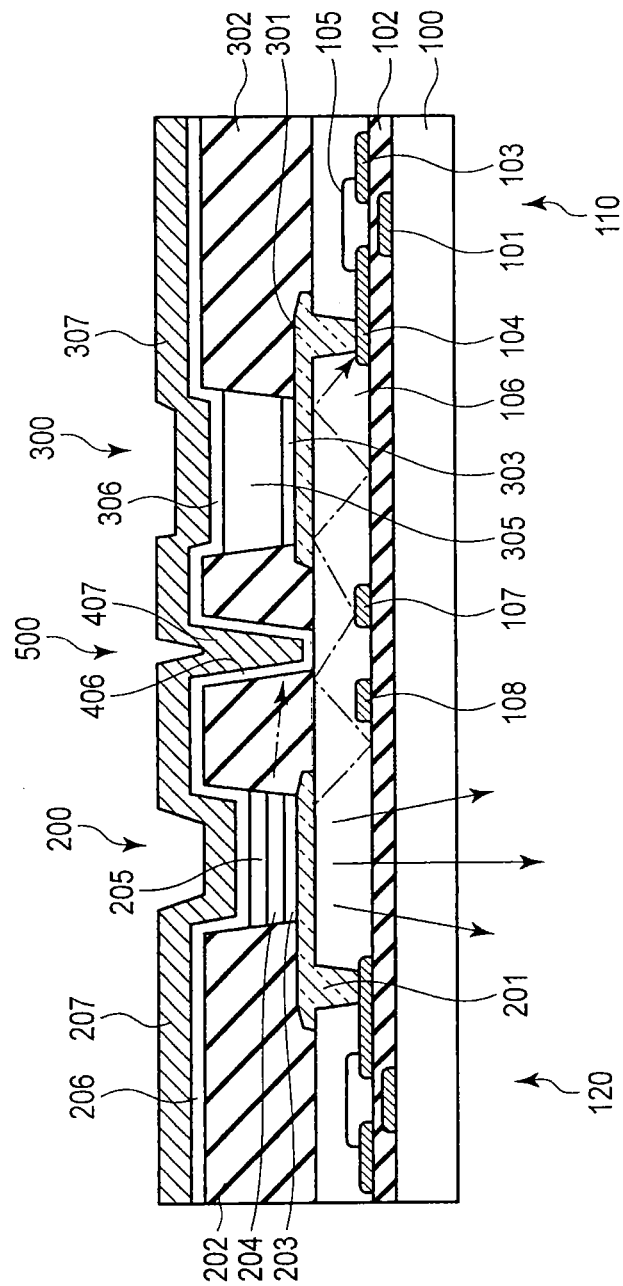
FIG. 6 is a sectional view showing the element structure of a light source-sensor integrated type photoelectric conversion device according to the second embodiment.
Figure 7:
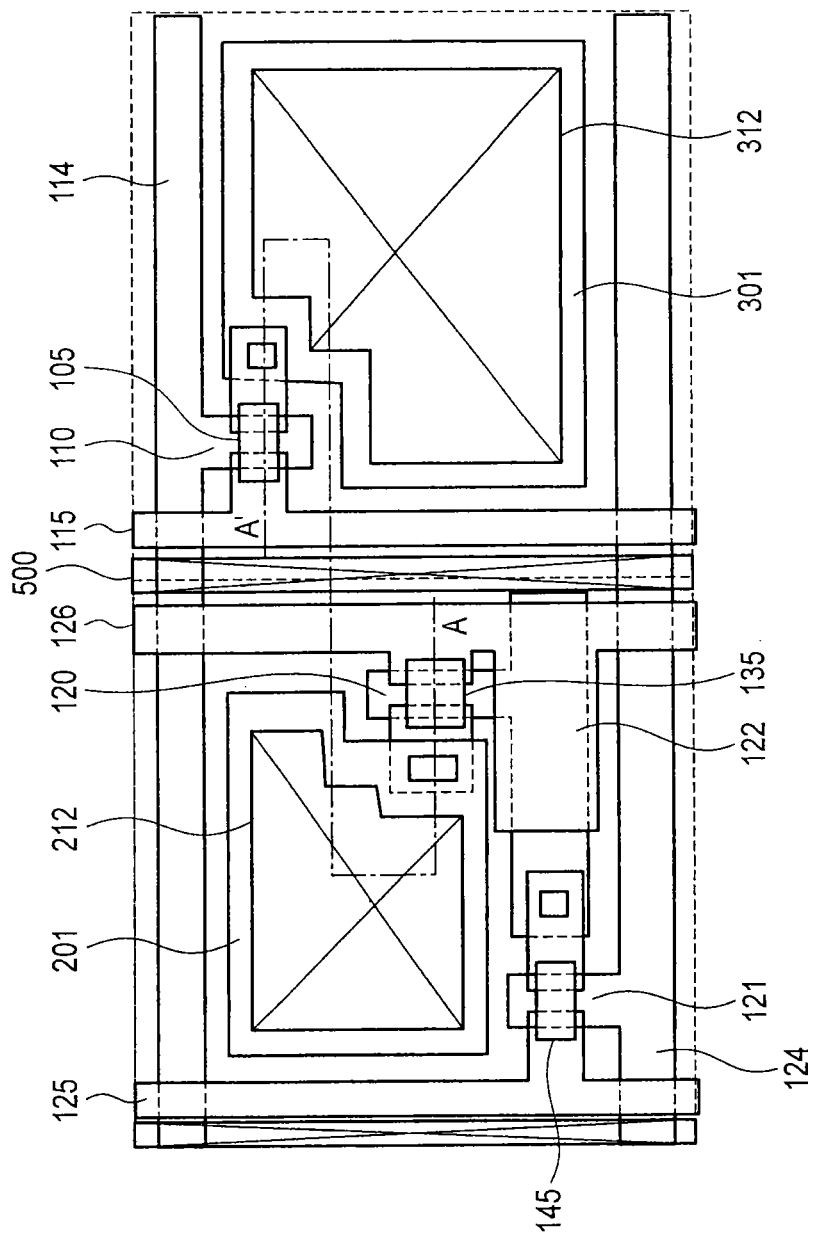
FIG. 7 is a view showing a planar layout of elements corresponding to the element structure shown in FIG. 6.

FIG. 6 shows the basic element structure of a photoelectric conversion device according to the second embodiment, and FIG. 7 shows a planar layout of the second embodiment. A section A-A' in FIG. 7 corresponds to FIG. 6. Note that the same reference numerals denote common portions as those in FIGS. 3 and 5, and a detailed description thereof will not be repeated.

This embodiment has a feature in that a bank trench 500 is formed between a light-emitting element 200 and light-receiving element 300, as shown in FIG. 6. Furthermore, the same structures 406 and 407 as common electron injection layers 206 and 306 and cathode electrodes 207 and 307 of the light-emitting element 200 and light-receiving element 300 are formed in the bank trench 500. Also, as shown in FIG. 7, the trench 500 is formed between a signal line 115 of the light-receiving element 300 and a power supply line 126 of the light-emitting element 200. By forming the bank trench 500 in this way, and forming the cathode electrode 407 in the trench 500, the cathode electrode 407 can reflect and absorb light from the light-emitting element 200. With this structure, light from the light-emitting element 200 can be greatly eliminated from reaching the light-receiving element 300, and weak light from an object can be detected with a high sensitivity without any noise. It is desirable to form the cathode electrode 407 (207, 307) using Al, Ag, or the like to have a thickness of 100 nm or more.

As shown in FIG. 7, the trench 500 preferably runs between a column of the light-emitting elements 200 and that of the light-receiving elements 300 so as to attain a light-shielding effect. FIG. 8 shows positions of the trenches 500 described in a pixel circuit. FIG. 8 does not illustrate detailed relationships such as overlaps between interconnections and the trenches 500. Also, FIG. 8 illustrates both the trenches which may or may not overlap interconnections. Note that the trenches 500 may be partially formed. By leaving a bank between the trench and scan line, an effect of reducing a parasitic capacitance can be obtained.

As described above, according to this embodiment, since light from the light-emitting element 200 is intercepted by the bank trench 500 formed between the light-emitting element 200 and light-receiving element 300, the light-receiving element 300 can be suppressed from being directly irradiated with light from the light-emitting element 200. For this reason, noise due to light rays (stray light rays) different from original response light from an object can be reduced, thus enhancing the detection sensitivity. Also, by burying, in the bank trench 500, the material (cathode electrode) 407 which absorbs or reflects light from the light-emitting element 200, the noise can be further reduced.

FIGS. 9A to 9J are process sectional views for explaining the manufacturing method of the photoelectric conversion device according to the second embodiment.

As shown in FIG. 9A, gate electrodes 101, scan lines, and the like are formed on a substrate 100 such as a plastic substrate, a hybrid substrate prepared by mixing glass fibers in an organic resin (a barrier layer and undercoat layer may be formed on the substrate or organic resin), or a glass substrate. Upon formation of them, a nano-Ag ink (a conductive ink dispersed with Ag nano-particles) may be printed, and may then be baked. After a conductive film such as MoTa or MoW may be formed by sputtering, a resist pattern may be formed by a normal photolithography process, and the conductive film may be etched using this resist pattern as a mask. In this case, after a 200-nm-thick MoW film was formed by sputtering, it was processed by dry etching.

As shown in FIG. 9B, after a gate insulating layer 102 is formed, predetermined contact holes are formed. More specifically, an organic layer such as polyimide, an acrylic resin, fluorine resin, partial fluorine resin, or polyvinyl phenol (PVP) is coated, and is then annealed. Then, after a resist pattern is formed, the resultant structure undergoes etching required to form contact holes. The gate insulating layer 102 may be locally coated by a print method. Furthermore, the gate insulating layer 102 having a photosensitivity may be formed, may be exposed and developed to form a pattern, and may then be cured by annealing. After an inorganic film such as SiOx may be formed by CVD or sputtering, contact holes may be formed by a photolithography process. Furthermore, as the gate insulating layer 102, inorganic and organic films may be stacked. In this case, after a photosensitive partial fluorine resin was coated and underwent an exposure/development treatment, it was annealed at 150° C., thus forming a film.

As shown in FIG. 9C, source/drain electrodes 103 and 104 and interconnections 107 and 108 such as a signal line and power supply line are formed to have desired patterns. In the same manner as the gate electrodes 101, these electrodes and interconnections can be formed using various methods and materials. In this case, after a nano-Ag ink (an Ag-nanoink) was coated to form desired patterns by printing, it was baked at 150° C., thus forming films.

As shown in FIG. 9D, a semiconductor layer 105 is formed by coating, deposition, CVD, or the like. The semiconductor layer 105 may be formed of either an organic or inorganic material. Upon forming this layer by printing, after a surface energy pattern may be formed, a material may be coated. That is, after patterns of lyophilic portions and lyophobic (liquid-repellent) portions are formed on the substrate surface, a semiconductor solution is printed on these patterns to leave the semiconductor solution on the lyophilic portion. Then, the semiconductor solution is dried to form a semiconductor pattern. The semiconductor solution may be coated after a bank pattern is formed. That is, the semiconductor solution is coated in the banks, thus printing a semiconductor material in portions partitioned by the banks. Then, the semiconductor material is dried to form a semiconductor pattern. In this case, although not shown, banks were exposed and developed using a photosensitive resin and were then annealed to form the banks, and a semiconductor was printed there to form a semiconductor pattern.

PFBT (Pentafluorobenzenethiol) SAM (self-assembled monolayer) or $F_4TCNQ$ layer, which enhances a work function of an Ag electrode of the source/drain electrode was formed by dipping in a solution. As an organic semiconductor, low molecular 6,13-bis(triisopropyl-silylethynyl)pentacene (TIPS-pentacene) or 2,7-dialkyl[1]benzothieno[3,2-b][1]benzothiophene (Cn-BTBT) was coated by an ink-jet method and dried, thus forming a film. A film thickness fell within a range from 10 to 1000 nm.

As shown in FIG. 9E, an insulating layer 106 used as a passivation film and interlayer dielectric film is formed on the structure shown in FIG. 9D, and a contact hole pattern is formed on the insulating layer 106. The insulating layer 106 may be either an organic or inorganic film, or may be formed by stacking both the films. In this case, after exposure and development using a photosensitive fluorine resin, a film was formed by annealing at 150° C. or less to have a thickness of 0.5 to 3 µm.

Figure 9F:
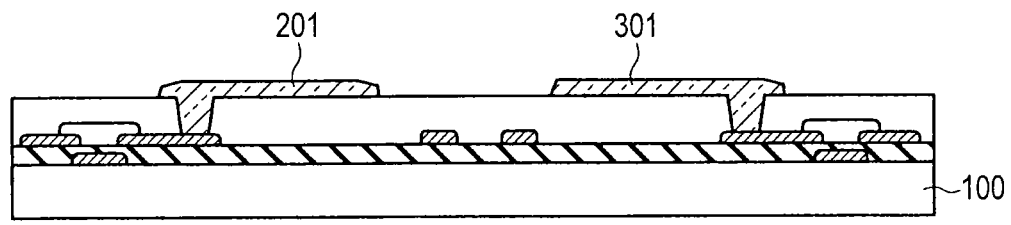

As shown in FIG. 9F, transparent conductive electrodes 201 and 301 of the light-emitting element 200 and light-receiving element 300 are formed. More specifically, after an ITO film is sputtered, it can be processed by etching by a photolithography process. After an ink dispersed with ITO particles or the like may be printed and coated, it may be annealed. In this case, after an ink dispersed with ITO nano-particles was printed, these electrodes were formed by annealing.

Figure 9G:
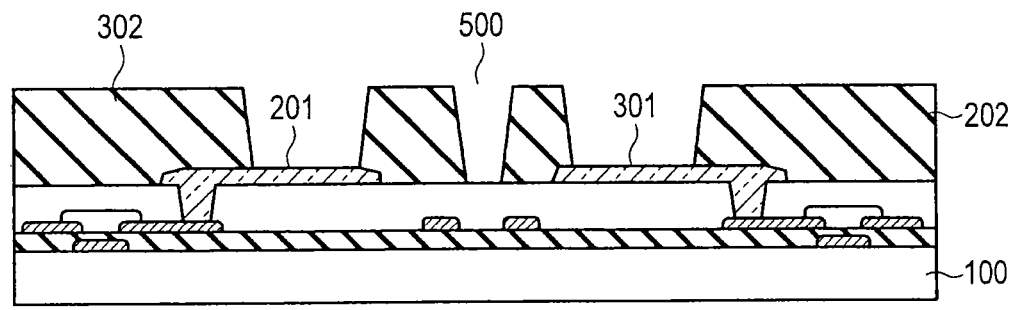

As shown in FIG. 9G, banks 202 and 302 made of an insulating film are formed on them, and openings of the banks 202 and 302 are formed to be located inside the transparent conductive electrodes 201 and 301. They may be formed by pattern printing or a photosensitive resin may be used. In this case, a photosensitive acrylic resin was used to set a film thickness ranging from 5 to 10 μm. Furthermore, a trench 500 is formed between the light-emitting element 200 and light-receiving element 300.

Figure 9H:
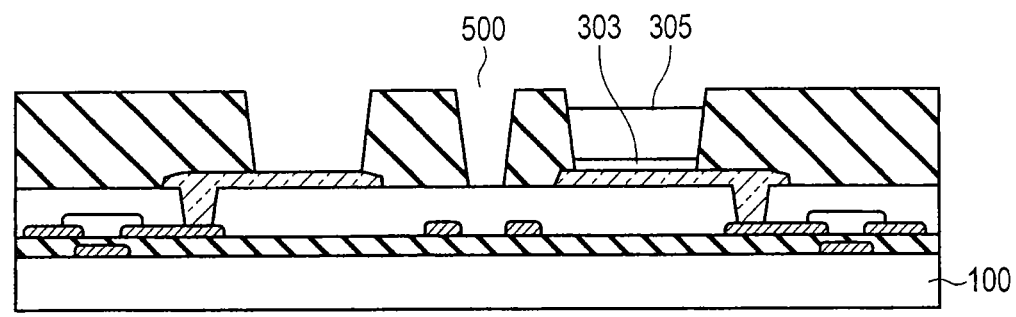

As shown in FIG. 9H, layers 303 and 305 including a light-receiving active layer of the light-receiving element 300 are formed in the opening of the bank on the light-receiving element side. As the hole injection layer 303, a film was formed by coating and drying PEDOT:PSS. In this case, the PEDOT:PSS may be formed in only the light-receiving element 300. However, the present invention is not limited to this, and it may also be formed as a hole injection layer in the light-emitting element 200. By forming common hole injection layers in the light-emitting element 200 and light-receiving element 300, electrode surfaces can easily undergo interface control (cleaning, work function control) by a plasma treatment. On the hole injection layer 303, as the light-receiving active layer 305, a p-type organic semiconductor and n-type organic semiconductor were respectively dissolved in a solvent, and were locally coated by an ink-jet system or a dispenser. After that, a bulk hetero-structure was formed by drying and annealing.

As a material having a sensitivity to near-infrared light, as a p-type semiconductor, poly{N-[1-(2-ethylhexyl)-3-ethylheptanyl]-dithieno[3,2-b:2',3'-d]pyrrole-3,6-dithien-2-yl-2,5-dibutylpyrrolo[3,4-c]pyrrole-1,4-dione-5',5"-diyl} (PDTP-DTDPP(Bu)) was used. The present invention is not limited to this, and poly{N-[1-(2-ethylhexyl)-3-ethylheptanyl]-dithieno[3,2-b:20,30-d]pyrrole-3,6-dithien-2-yl-2,5-di(2-ethylhexyl)-pyrrolo[3,4-c]pyrrole-1,4-dione-50,500-diyl} (PDTP-DTDPP) may be used. As an n-type semiconductor, PCBM fullerene or PC70BM may be used.

FIGS. 29A to 29D show molecular structures of them. PDTP-DTDPP(Bu) is a material which has a HOMO-LUMO difference=1.27 eV, and absorbs near-infrared light. As a sensitivity in an element, an external quantum efficiency EQE of 20% or more can be obtained up to a wavelength of 1100 nm, and in particular, at 700 to 900 nm. As a solvent, a mixed solvent of chloroform and o-dichlorobenzene (a volume ratio=4:1) was used. However, an appropriate solvent which can obtain properties in an organic material and underlying substrate may be selected.

The film thickness of the active layer 305 was set to be 1 to 10 μm. As is known, a dark current can be reduced by increasing the film thickness. By increasing the film thickness, a reduction of a difference from a signal at a light irradiation timing as a result of accumulation of electric charges on the light-receiving element 300 due to a dark current can be prevented. Especially, by setting a film thickness of 2 μm or more, a dark current can be sufficiently reduced, and a sensitivity drop can be prevented. On the other hand, when the film thickness is increased, since sensitivity to light from the light-emitting element 200 in the lateral direction is enhanced, noise due to stray light tends to increase. Therefore, the light-shielding effect of the bank trench 500 in the structure of the second embodiment can be more enhanced (to reduce any leakage). The bulk hetero-structure can be formed by annealing at 120° C. Note that as the light-receiving element 300, a multilayered structure of p- and n-type semiconductors may be formed according to wavelengths and sensitivities.

Figure 9I:
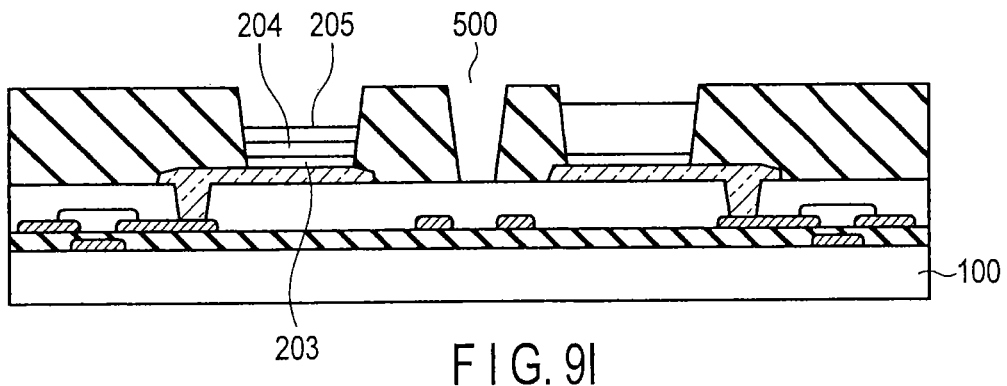

As shown in FIG. 9I, layers 203, 204, and 205 including a light-emitting layer of the light-emitting element 200 are formed. In this case, PEDOT:PSS was used as the hole injection layer 203. The light-emitting layer 205 was caused to emit a near-infrared wavelength (near a peak wavelength of 780 nm) by doping Pt-tetraphenyltetrabenzoporphyrin (Pt (tpbp)) in a host layer which was prepared by mixing PVK and OXD-7 to enhance its electron transport.

As another configuration, PEDOT:PSS or $MoO_3$ was used as the hole injection layer 203, and NPB was used as the hole transport layer 204. As the light-emitting layer 205, a predetermined dopant was introduced using $Alq_3$ as a host layer. Furthermore, BCP was used as a hole blocking layer, and $Alq_3$ was used as an electron transport layer. The dopant used was obtained by coupling triphenylamine- and benzobis (thiadiazole)-based materials (a wavelength was changed around a peak wavelength ranging from 750 to 850 nm by the dopant material and concentration). In this case, light emission caused by recoupling occurs by injecting electron-hole pairs into a host material having a large HOMO-LUMO band gap and by moving carriers to a HOMO-LUMO level of a dopant.

Figure 30A:
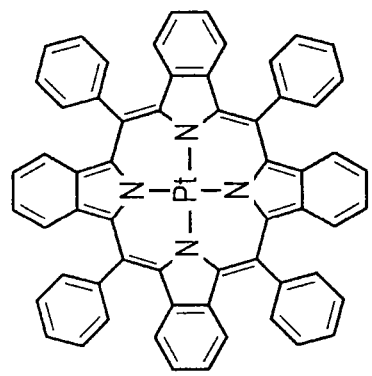
FIGS. 30A and 30B are views showing the molecular structures of doping materials used in a light-emitting layer of the photoelectric conversion device of the second embodiment.
Figure 30B:
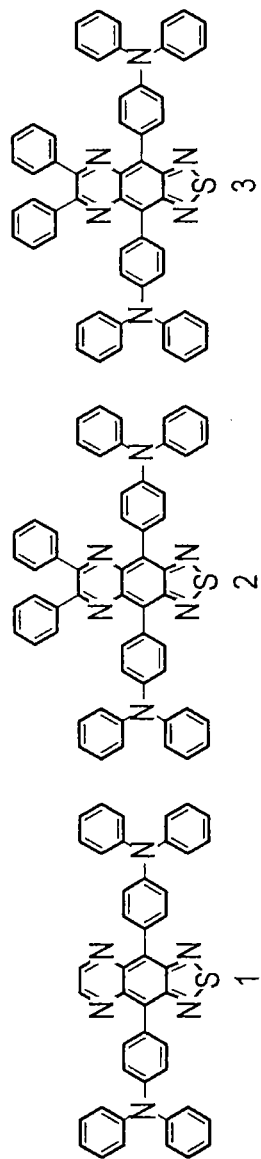

When such materials are used as the light-receiving element 300, nearly no sensitivity of the light-receiving element is obtained. However, when the light-emitting element and light-receiving element are independently configured as in this embodiment, a very weak signal like information from a living body can also be obtained. The respective layers 203 to 205 of the light-emitting element 200 may be formed by deposition, or may be partially formed by coating. These organic light-emitting elements have a susceptibility to annealing. When annealing (for example, 120° C.) required to form the bulk hetero-structure of the light-receiving element 300 is executed before film formation of the light-emitting element 200, deterioration of the light-emitting element 200 due to annealing can be prevented. Note that the hole transport layers may be simultaneously formed in the light-emitting element 200 and light-receiving element 300. FIGS. 30A and 30B show structures of doping materials suited to near-infrared light emission.

Figure 9J:
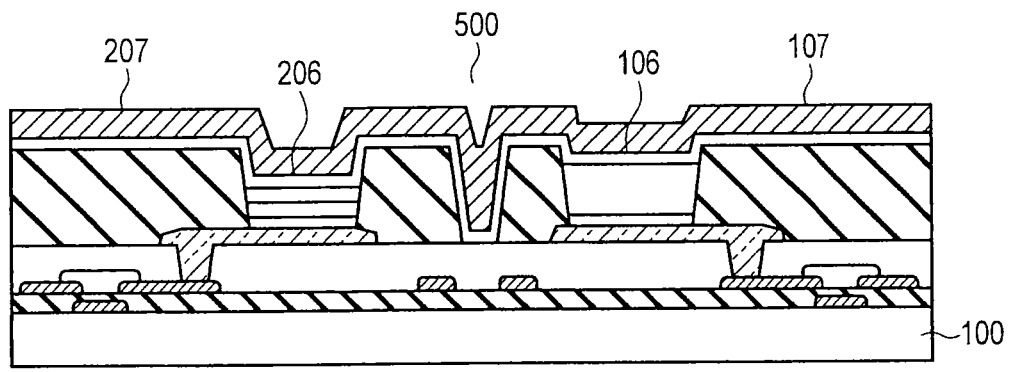

Finally, as shown in FIG. 9J, common electron injection layers 206 and 306 and cathode electrodes 207 and 307 of the light-emitting element 200 and light-receiving element 300 are formed. In this case, the electron injection layer was formed of LiF, CsF, or the like, and the cathode electrode was formed of Al. The Al film thickness was set to fall within a range from 100 nm to 3 μm. As the film thickness is larger, the light-shielding property of the trench 500 is enhanced, a resistance can also be reduced, and water permeation before sealing is reduced, thus suppressing process deterioration. Although not described in this embodiment, sealing is done after electrode formation. At this time, since the electrodes of the light-emitting element 200 and light-receiving element 300 are formed at the same time, sealing can be done while suppressing element deterioration.

As described above, according to this embodiment, optimal materials and configurations of the light-emitting element 200 and light-receiving element 300 can be selected, and a very weak signal can be obtained in response to near-infrared light. Note that this manufacturing method is applicable to other embodiments.

Third Embodiment

Figure 10:
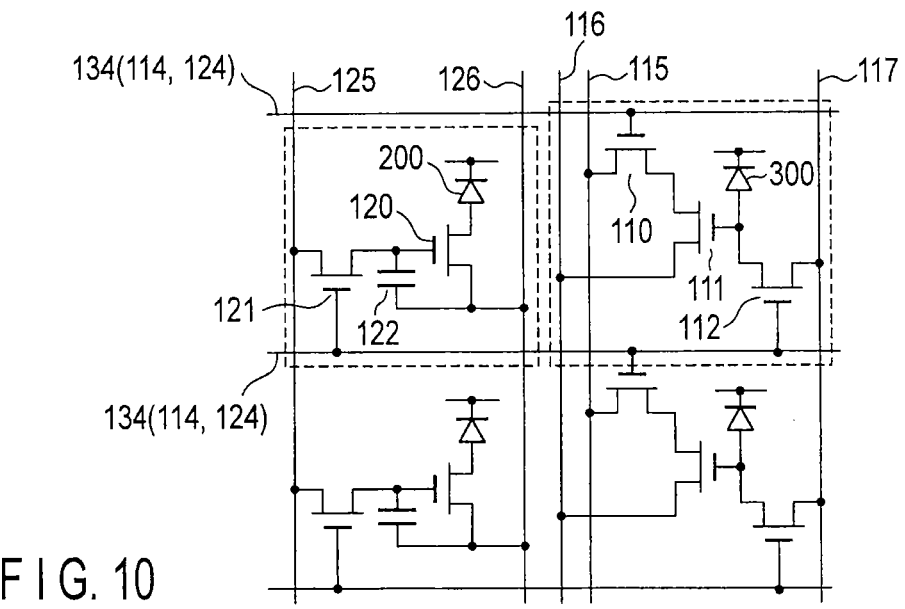
FIG. 10 is a circuit diagram showing the circuit arrangement of a pixel unit of a light source-sensor integrated type photoelectric conversion device according to the third embodiment.
Figure 11:
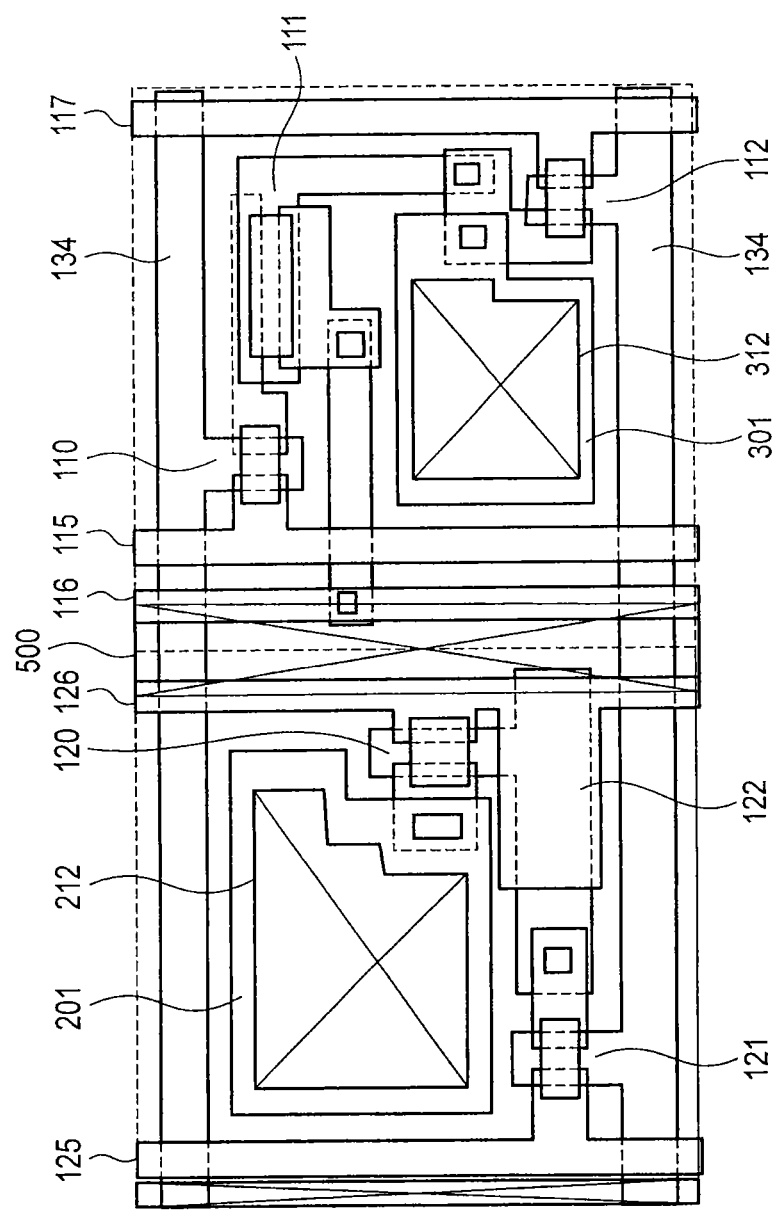
FIG. 11 is a view showing a planar layout of elements corresponding to the circuit arrangement shown in FIG. 10.

FIG. 10 shows the circuit arrangement of a pixel unit of a photoelectric conversion device according to the third embodiment, and FIG. 11 shows a layout of the pixel unit.

In this embodiment, an active type amplifier is arranged as a detection circuit of a light-receiving element 300. One electrode of the light-receiving element 300 is connected to the gate of an amplifier thin-film transistor 111 of a source follower, and the source electrode of the transistor 111 is connected to a power supply line 116. The drain electrode of the transistor 111 is connected to a signal line 115 via a switching transistor 110. The gate of the switching transistor 110 is connected to a scan line 134. The transistor 110 supplies a current to the signal line 115 when it is enabled after the scan line 134 goes to high level. In this case, electric charges according to incident light on the light-receiving element 300 set a gate voltage of the amplifier transistor 111. Then, a voltage lower by about Vth is supplied to the signal line 115 via the switching transistor 110.

With this arrangement, a charge amount flowing through the signal line 115 can be a large charge amount in correspondence with the size and on-current of the transistor compared to the above amplifier-less circuit shown in FIG. 4. Thus, the influence of external noise can be suppressed. This is effective especially for a living body sensor, which is used while being in tight contact with or being wearably adhered to a human body. Note that in case of the amplifier type, electric charges on the light-receiving element 300 cannot be returned to a constant voltage even after they are read. For this reason, a reset transistor 112 is connected to the light-receiving element 300 to set a voltage of a reset signal line 117 at a high-level timing of another scan line 134. Thus, a read operation can be repetitively executed. The circuit and arrangement on the light-emitting element side are equivalent to those in FIGS. 4 and 5.

In this case, read scan lines 114 of the light-receiving elements 300 which vertically neighbor pixels are used. For this reason, during a time period from when the light-receiving element 300 is reset after electric charges are read until the next read operation, the light-receiving element 300 accumulates electric charges. The read scan line 114 is commonly used as a write scan line 124 of the light-emitting element 200. In this manner, by reducing the number of scan lines 134, an area in each pixel can be increased. It is effective to increase the effective areas of the light-emitting element 200 and light-receiving element 300, and to enhance the detection sensitivity and emission intensity. Note that the common scan lines 134 are applicable to other embodiments. In the amplifier type like in this embodiment, the scan lines 114 and 124 can be independent signal lines without being commonized. Furthermore, an independent read scan line and reset scan line can also be used. By adopting these interconnections as independent ones, timings can be freely controlled, thus effectively attaining sensitivity adjustment and noise reduction.

In this embodiment, a trench 500 is further formed between a bank (pixel boundary 212) of the light-emitting element 200 and that (pixel boundary 312) of the light-receiving element 300. A common cathode electrode 407 and electron injection layer 406 of the light-emitting element 200 and light-receiving element 300 are formed in the bank trench 500, thus further enhancing the light-shielding property. With this structure, entrance of light to the light-receiving element 300 can be suppressed, thereby reducing noise.

The bottom surface of the trench 500 is designed to overlap a power supply line 126 of the light-emitting element 200. With this structure, even when light with which the side surface of the trench 500 is irradiated is reflected in a substrate direction, it is intercepted by the power supply line 126, and emerges as light in only a downward direction. For this reason, stray light to the light-receiving element 300 can be suppressed. Furthermore, in this embodiment, the power supply line 116 of the light-receiving element 300 is laid out in the neighborhood of the power supply line 126 of the light-emitting element 200. At this time, since the bottom surface of the trench 500 is designed to overlap the power supply line 116 of the light-receiving element 300, the width of the trench 500 can be increased. For this reason, the working precision is relaxed to allow easy manufacture. Furthermore, even when an insulating layer between the power supply line as an electrode which is free from or suffers less potential variations and the cathode electrode is thinned, the cathode electrode is free from the influence of a parasitic capacitance, and suffers less noise and less variations. The overlapping between the trench 500 and the power supply line 116 on the light-receiving element side can also intercept an incident route of stray light, thus providing an optical noise reduction effect. FIG. 12 shows the global relationship between the trenches 500 over a plurality of pixels and pixel circuits.

Figure 13:
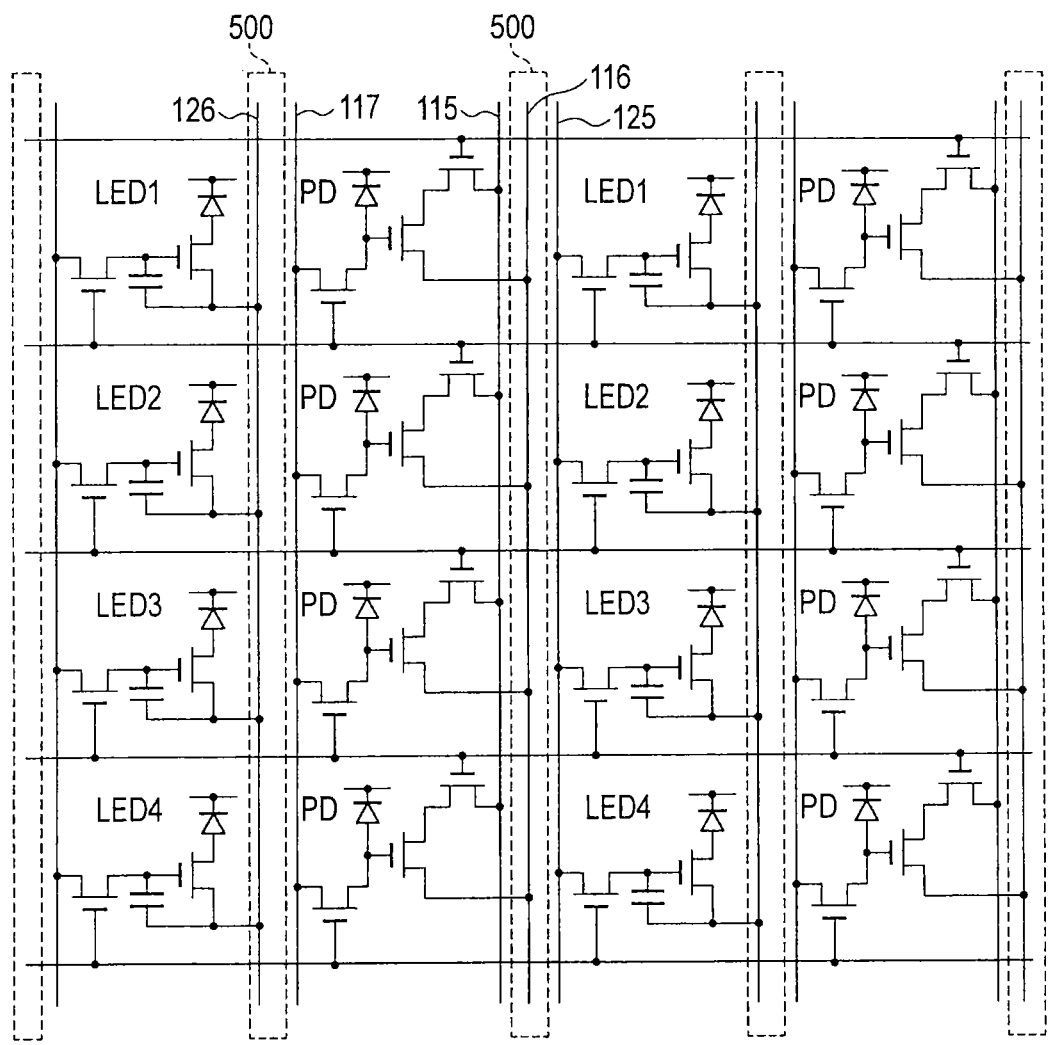
FIG. 13 is a view showing another example of the relationship between pixel units and trenches in the photoelectric conversion device shown in FIG. 10.

Note that the power supply line 116 of the light-receiving element 300 may be arranged on the right side of FIGS. 10 and 11 opposite to the position in FIGS. 10 and 11. Then, as a trench layout when the light-receiving element 300 is laid out on the left side of the light-emitting element 200, the trench can overlap the power supply line of the light-receiving element 300. In this case, the same effect as the overlapping of the power supply line on the light-emitting element side can be obtained. FIG. 13 shows the global relationship between pixels and the trenches 500. Power supply lines which are free from voltage variations are laid out between neighboring columns of the light-emitting elements 200 and light-receiving elements 300. For this reason, even when each trench 500 is laid out to overlap the interconnection, a layout which suffers less the influence of a parasitic capacitance is allowed. By overlapping each trench 500 on the interconnection, a light-shielding effect is enhanced.

Fourth Embodiment

Figure 14:
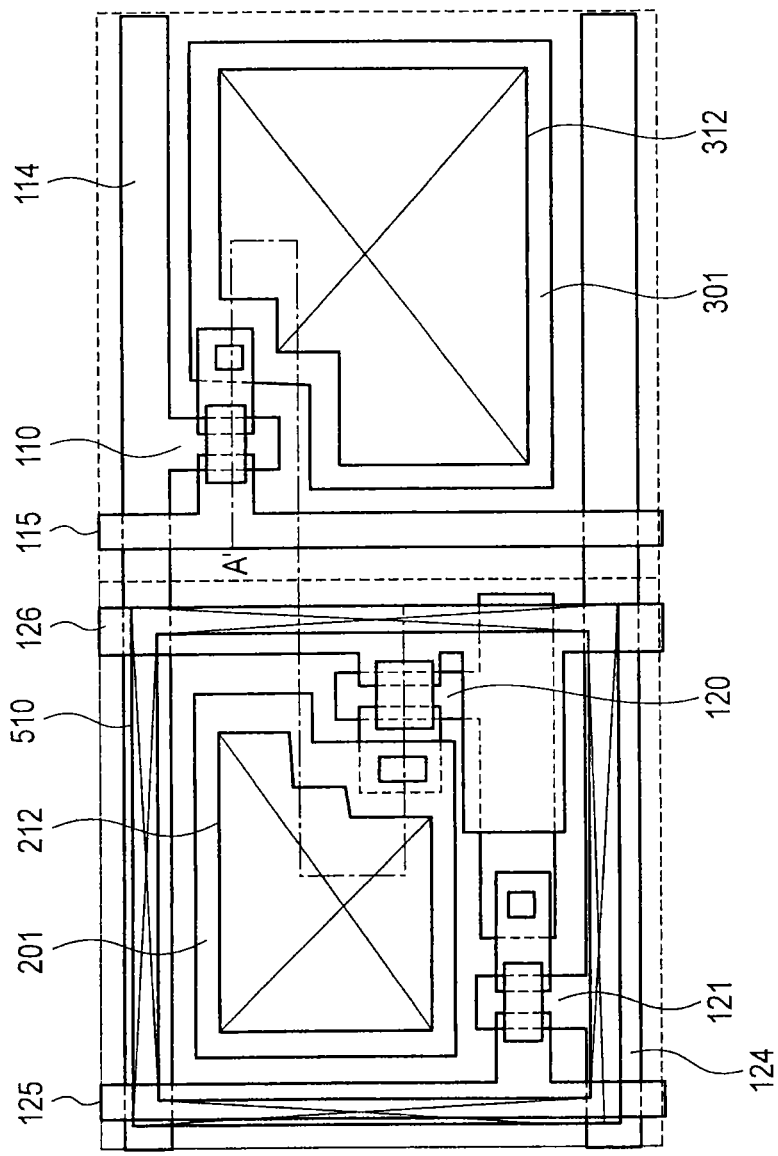
FIG. 14 is a view showing a planar layout of a pixel unit of a light source-sensor integrated type photoelectric conversion device according to the fourth embodiment.
Figure 15:
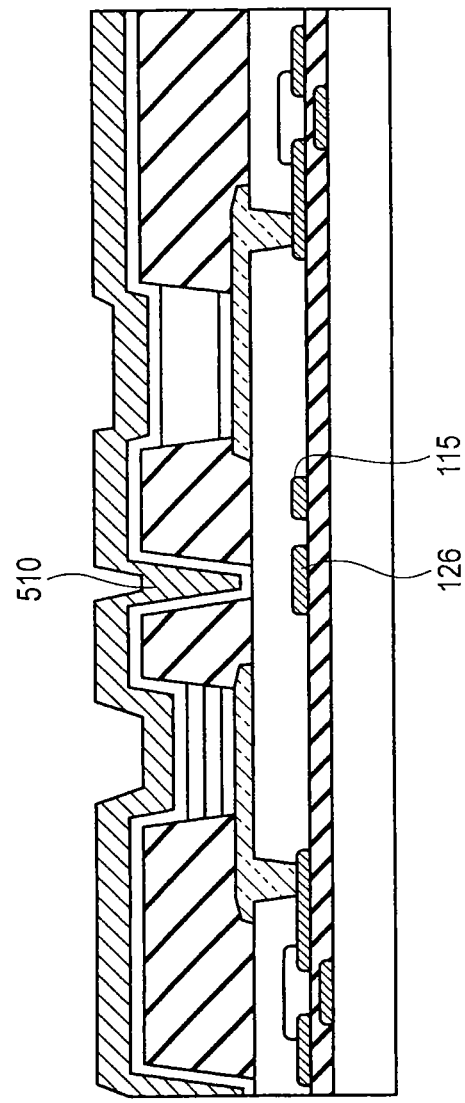
FIG. 15 is a sectional view showing the element structure in the photoelectric conversion device shown in FIG. 14.

FIG. 14 shows a planar layout of a pixel according to the fourth embodiment, and FIG. 15 shows a section A-A' of FIG. 14.

In this embodiment, a layout of a trench of banks is devised. This embodiment has a feature that a trench 510 is laid out on the outer periphery of a light-emitting element 200, and the bottom surface of the trench 510 overlaps an electrode (power supply line) 126 of an active matrix. The trench 510 overlaps the electrode 126 at a position between the light-emitting element 200 and light-receiving element 300. The electrode 126 suppresses light with which the side surface of the trench 510 is irradiated from emerging in an oblique direction when it is reflected in a substrate direction. Thus, stray light which reaches the light-receiving element 300 can be suppressed, thus reducing noise caused by leakage.

Figure 16:
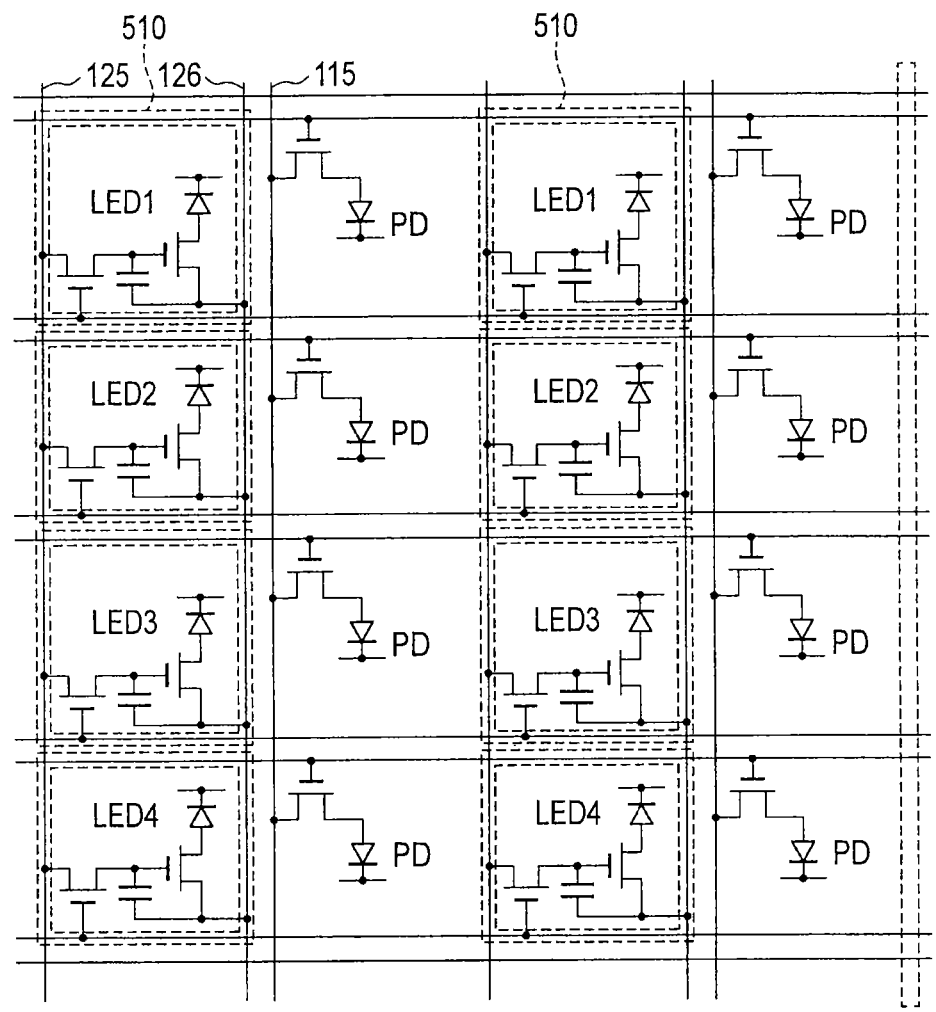
FIG. 16 is a view showing the relationship between pixel units and trenches in the photoelectric conversion device shown in FIG. 14.

In FIGS. 14 and 15, an interconnection overlapped by the trench 510 is the power supply line 126. Instead, a scan line and signal line can also be used. Using matrix intersections of them, the trench can be laid out to surround the outer periphery of the light-emitting element unit, thus improving the light-shielding effect. FIG. 16 illustrates the relationship between the trenches 510 and pixel circuits.

Figure 17:
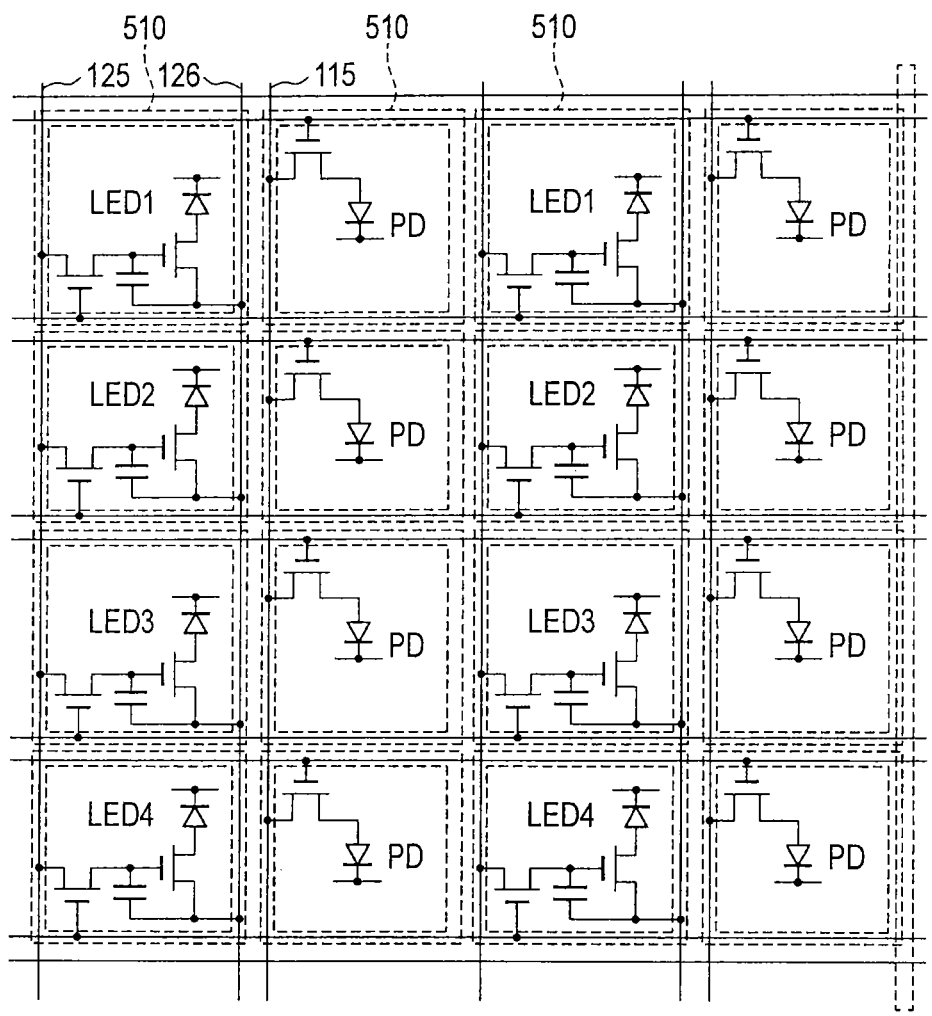
FIG. 17 is a view showing another example of the relationship between pixel units and trenches in the photoelectric conversion device shown in FIG. 14.
Figure 18:
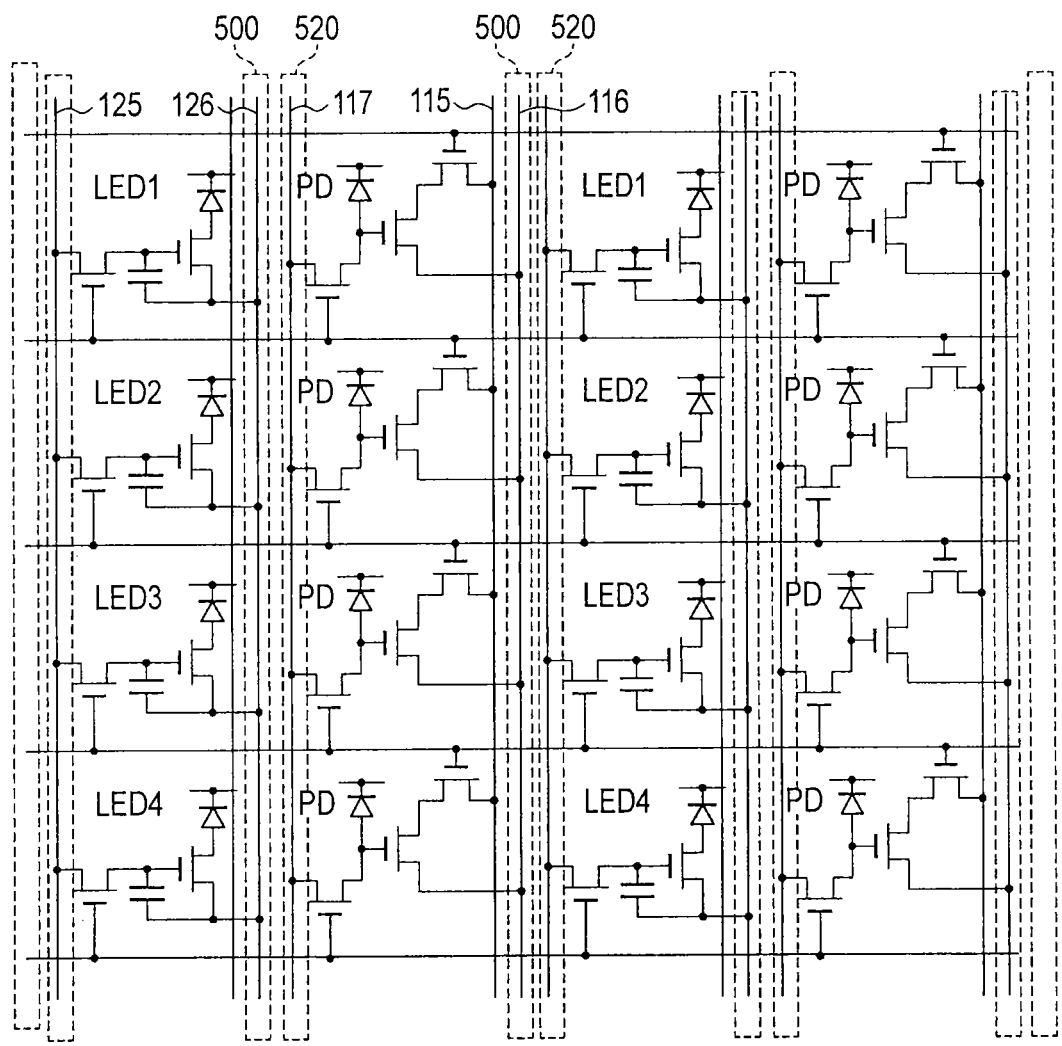
FIG. 18 is a view showing still another example of the relationship between pixel units and trenches in the photoelectric conversion device shown in FIG. 10.

As a layout of the trench 510, multiple trenches 510 can be formed. FIG. 17 shows the multiple layout of the trenches 510 also on the light-receiving element side in the fourth embodiment. In FIG. 18, trenches 520 are further added to the layout shown in FIG. 13. By arranging the multiple trenches, the light-shielding effect can be enhanced, and noise reduction and impedance matching effects can also be attained.

The trench may be partially formed. The light-shielding effect may be obtained or a portion corresponding to a high intensity may be shielded by devising the relationship between trenches. In FIG. 19, for example, trenches 530 are intermittently formed in the vicinity of signal lines of the light-receiving elements 300. Since no trench 530 is formed on an overlapping portion with a scan line, a delay of a scan signal can be reduced, and a large potential change of the scan signal can be suppressed from being superposed on a common electrode as noise. A trench 540 is formed on each overlapping portion between a power supply line and scan line, thus suppressing generation of a parasitic capacitance due to overlapping with the scan line. A trench 550 which extends along a power supply line on the light-receiving element side runs over the entire surface, and these trenches can obtain the light-shielding effect.

As described above, multiple trenches 510 may be formed between the light-emitting elements 200 and light-receiving elements 300, and a portion without any trench 510 can be compensated for by another portion.

Fifth Embodiment

Figure 20:
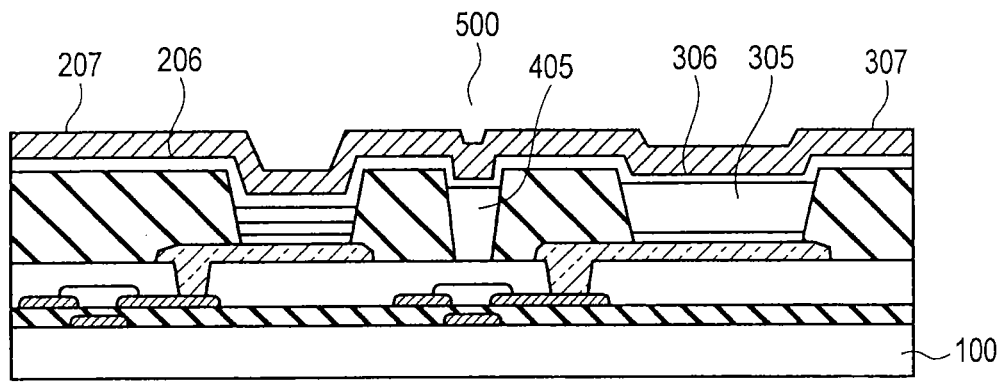
FIG. 20 is a sectional view showing the basic element structure of a light source-sensor integrated type photoelectric conversion device according to the fifth embodiment.

FIG. 20 shows the basic element structure of a photoelectric conversion device according to the fifth embodiment.

This embodiment has a feature that a layer 405 including a light-receiving active layer 305 of a light-receiving element 300 is formed in a bank trench 500 laid out between a light-emitting element 200 and the light-receiving element 300. The light-receiving active layer has characteristics for absorbing light of a light-receiving sensitivity wavelength. For this reason, by forming the light-receiving active layer in the bank trench 500, a light-shielding effect can be obtained by absorbing stray light. The light-receiving active layer is a semiconductor layer which is formed to have a thickness as large as 1 to 10 µm. Since the light-receiving active layer is formed of a semiconductor, it electrically has a lower conductivity than a metal, and coupling due to an electrostatic capacitance with the underlying active layer is reduced. Thus, a restriction of the layout position of the trench 500 can be relaxed.

This embodiment is also effective when common electrodes 207 and 307 of the light-emitting element 200 and light-receiving element 300 are formed of semitransparent materials to also output light on the side opposite to a substrate 100. That is, even when the light-shielding effect of the electrodes is reduced using the semitransparent electrodes, the influence of stray light can be suppressed by absorption of the light-receiving active layer.

Sixth Embodiment

Figure 21:
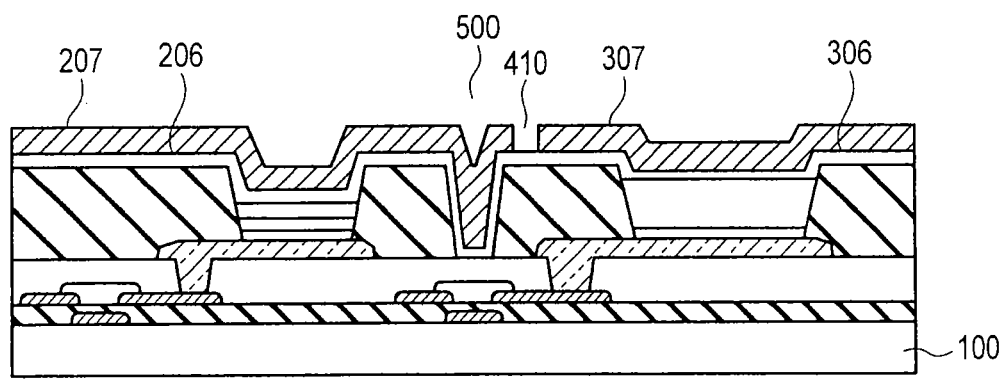
FIG. 21 is a sectional view showing the element structure of a light source-sensor integrated type photoelectric conversion device according to the sixth embodiment.

FIG. 21 shows the basic element structure of a photoelectric conversion device according to the sixth embodiment.

This embodiment has a feature that common electrode layers are not continuously formed for a light-receiving element 300 and light-emitting element 200, and a pattern which isolates a region of the light-receiving element 300 and that of the light-emitting element 200 is formed. That is, an electrode layer 207 of the light-emitting element 200 and an electrode layer 307 of the light-receiving element 300 are isolated from each other by forming a gap 410. Such structure can be realized by mask deposition upon forming the electrode layers.

With this structure, the influence of variations of a cathode electrode potential of the light-receiving element 300 due to a current flowing through the light-emitting element 200 can be prevented, thus facilitating detection of very weak variations. This structure is applicable to cases of a broad pixel region and low conversion efficiency of the light-emitting element. Note that as for whether the electrode is isolated or is formed on the entire surface, an appropriate method can be selected depending on materials and device design.

Seventh Embodiment

Figure 22:
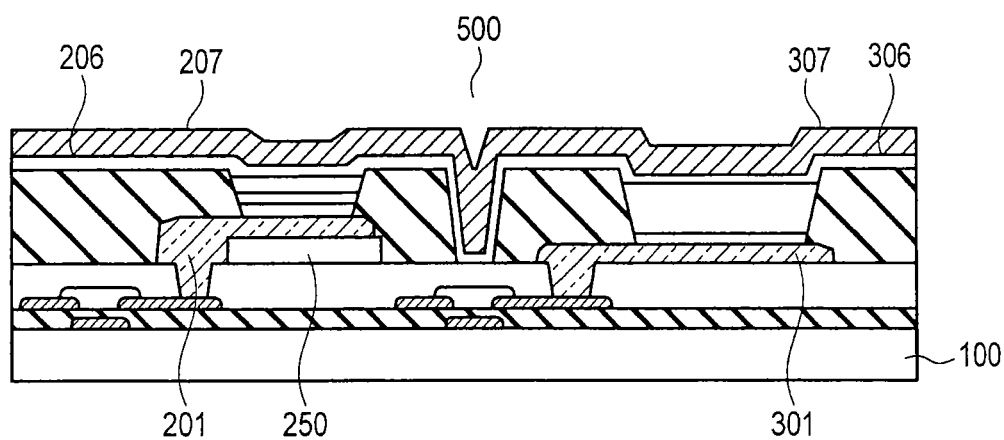
FIG. 22 is a sectional view showing the element structure of a light source-sensor integrated type photoelectric conversion device according to the seventh embodiment.

FIG. 22 shows the basic element structure of a photoelectric conversion device according to the seventh embodiment.

This embodiment exemplifies the structure of a light-emitting element 200 including an optical function layer 250. One example of the optical function layer 250 is a color filter which limits transmission wavelengths, and another example is an extraction mechanism member including microlenses which enhance light extraction. The optical function layer 250 is preferably formed below a lower electrode 201 of the light-emitting element 200. Furthermore, the optical function layer 250 is covered by a bank layer, thus effectively obtaining a light-shielding effect even when a trench 500 of the bank layer is formed.

Eighth Embodiment

FIG. 23 shows the basic element structure of a photoelectric conversion device according to the eighth embodiment.

In this embodiment, the embodiment shown in FIG. 20 is improved. This embodiment adopts a top emission/top reception structure, and a semitransparent electrode 607 such as a thin-film MgAg alloy is formed as a common electrode. In this case, since a sheet resistance of the electrode becomes high, a voltage drop in the electrode is caused by a current for emission. For this reason, such voltage drop causes an emission intensity nonuniformity, and influences a bias potential applied to the electrode common to the light-receiving layer. Also, that voltage drop causes a light-receiving sensitivity nonuniformity. Especially, when a device size is large, for example, when the device is wrapped around the arm to obtain signals over a broad range, a problem is posed.

Hence, this embodiment has a feature that electrodes 601 and 602 are formed on a counter substrate 600 to sufficiently reduce a resistance. An auxiliary interconnection 601 required to attain a resistance reduction, and a transparent low-resistance electrode 602 which is connected to the interconnection 601 and is made up of ITO or the like are formed on the substrate 600 which also serves as a protection/sealing substrate. Then, this transparent low-resistance electrode 602 is adhered to a light-emitting/light-receiving element substrate via an adhesive layer 603. The semitransparent electrode 607 of the light-emitting/light-receiving element substrate is electrically connected to the electrodes 601 and 602 of the counter substrate 600 by an entire in-plane surface or locally. Thus, their connection resistance can be greatly reduced to suppress a voltage drop in the semitransparent electrode 607. The adhesive layer 603 desirably has a conductive structure, for example, an adhesive material dispersed with transparent conductive particulates. Alternatively, a convex portion of the counter electrode may be in direct contact with and connected to the semitransparent electrode 607, and a gap is filled with an adhesive layer to fix them, thus obtaining the same effect.

Note that a trench 500 formed between the light-emitting element and light-receiving element on the light-emitting/light-receiving element substrate is preferably filled with a layer 405 containing a light-receiving active layer as a principal component as in FIG. 2. However, the present invention is not limited to this, and another trench structure may be combined.

Ninth Embodiment

Figure 24:
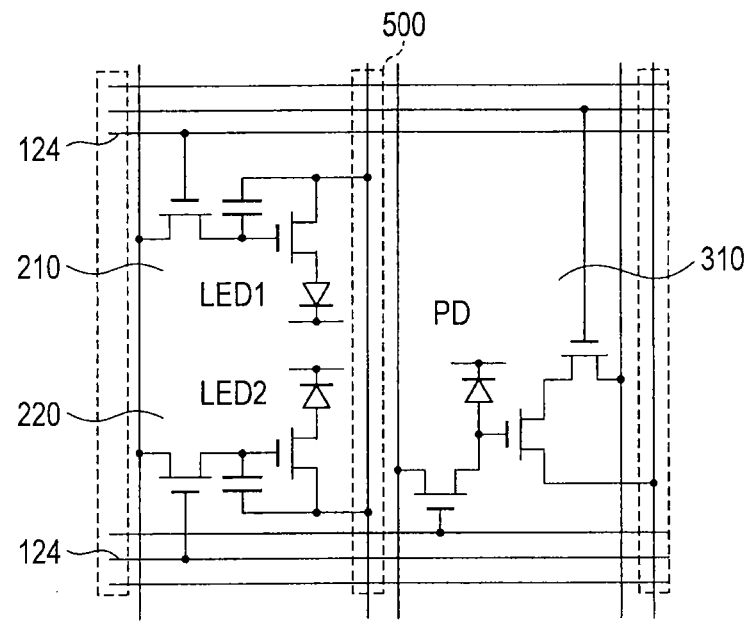
FIG. 24 is a circuit diagram showing the circuit arrangement of a pixel unit in a light source-sensor integrated type photoelectric conversion device according to the ninth embodiment.

FIG. 24 shows the circuit arrangement of a pixel unit in a photoelectric conversion device according to the ninth embodiment.

In this embodiment, pixels 210 and 220 of a light-emitting element 200, and a pixel 310 of a light-receiving element 300 have different pixel sizes. A width defined by stacking the pixels 210 and 220 of the light-emitting element 200 in a scanning direction sets a scanning direction pitch of the pixel 310 of the light-receiving element 300. The light-emitting element pixels include light-emitting elements LED1 and LED2 having different emission wavelengths. As information of near-infrared light of a living body, for example, upon irradiation of light rays of wavelengths=760 and 840 nm, signals corresponding to amounts of oxyhemoglobin and deoxyhemoglobin are obtained. From these signals, hemoglobin states can be detected under the assumption that routes of light rays from light-emitting elements pass through an identical portion in correspondence with two wavelengths. Therefore, it is effective to lay out the light-emitting elements of the two wavelengths at neighboring positions like in this embodiment. In addition, the spatial resolution of the light-receiving element need only be set for the two wavelengths. Therefore, with the layout shown in FIG. 24, a large light-receiving area can be assured, and the detection sensitivity can be improved. Especially, by vertically dividing a scan line 124 of the light-emitting element 200 with respect to the pixels, no scan line need not run through the light-receiving element pixel. This structure is suited to increase the light-receiving area.

Since a trench 500 need only be formed for the light-receiving element 300, it need only be formed between each column of light-emitting elements 200 and that of light-receiving elements 300. It is more preferable to lay out respective trenches 500 to partially or fully overlap power supply lines of the light-emitting elements 200 and light-receiving elements 300. The same relationship with interconnections can be adopted as in other embodiments.

Tenth Embodiment

Figure 25:
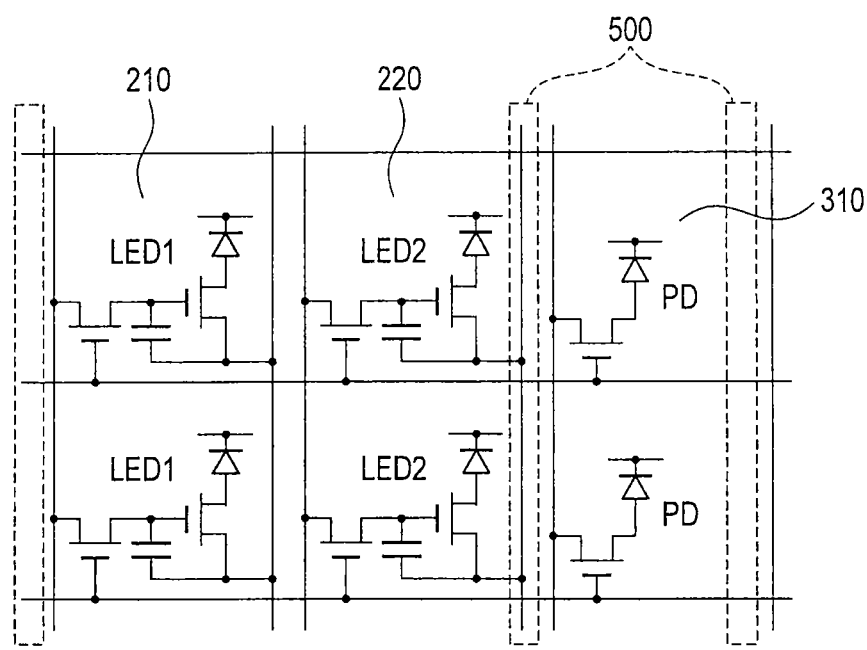
FIG. 25 is a circuit diagram showing the circuit arrangement of a pixel unit in a light source-sensor integrated type photoelectric conversion device according to the 10th embodiment.

FIG. 25 shows the circuit arrangement of a pixel unit in a photoelectric conversion device according to the 10th embodiment.

In this embodiment, pixels 210 and 220 of a light-emitting elements 200 having different wavelengths are laid out at neighboring positions in a direction along a signal line. A pixel 310 of a light-receiving element 300 is laid out in correspondence with these pixels. That is, the plurality of light-emitting elements 200 are laid out to be juxtaposed, and the light-receiving element 300 is laid out beside these elements. Such layout is desirably adopted when the sensitivity of the light-receiving element 300 is sufficient but the emission efficiency of each light-emitting element 200 is relatively low, or when the service life is prolonged by reducing current densities of the light-emitting elements 200.

Upon obtaining living body information, as shown in FIG. 2, light rays received by most neighbor pixels can provide only shallow information, and light-receiving signals of separated pixels are analyzed to obtain deeper information. In this case, the aforementioned light-emitting element array may be used, and correction for positions may be executed as needed.

A trench 500 need only be formed in the light-receiving element 300. Since no trench 500 is formed between the light-emitting elements 200, a degree of freedom in layout and aperture ratio can be improved.

Eleventh Embodiment

FIG. 26 shows the circuit arrangement of a pixel unit in a photoelectric conversion device according to the 11th embodiment.

This embodiment shows an arrangement required to mainly calibrate deterioration of an emission intensity of a light-emitting element 200 as well as aging of a light-receiving element 300. A monitor light-receiving element 350, which measures light from the light-emitting element 200 inside the substrate without emerging it outside the substrate, is arranged in correspondence with the light-receiving element 300 which receives reflected light of light which is emitted by the light-emitting element 200 and emerges outside the substrate. Feedback control may be executed based on a light-receiving signal of the monitor light-receiving element 350 to control a current to the light-emitting element 200 so as to obtain the same intensity. Alternatively, a signal of the light-receiving element 300 may be corrected based on a signal of the monitor light-receiving element 350. Furthermore, a trench 510 formed around the light-receiving element 300 suppresses stray light to the light-receiving element 300, thereby enhancing sensitivity. At this time, an optical coupling structure 700 between the monitor light-receiving element 350 and light-emitting element 200 is separated away from the trench 510. Thus, even when the light-emitting element 200 suffers deterioration, information from a living body can be acquired with high precision.

Figure 27:
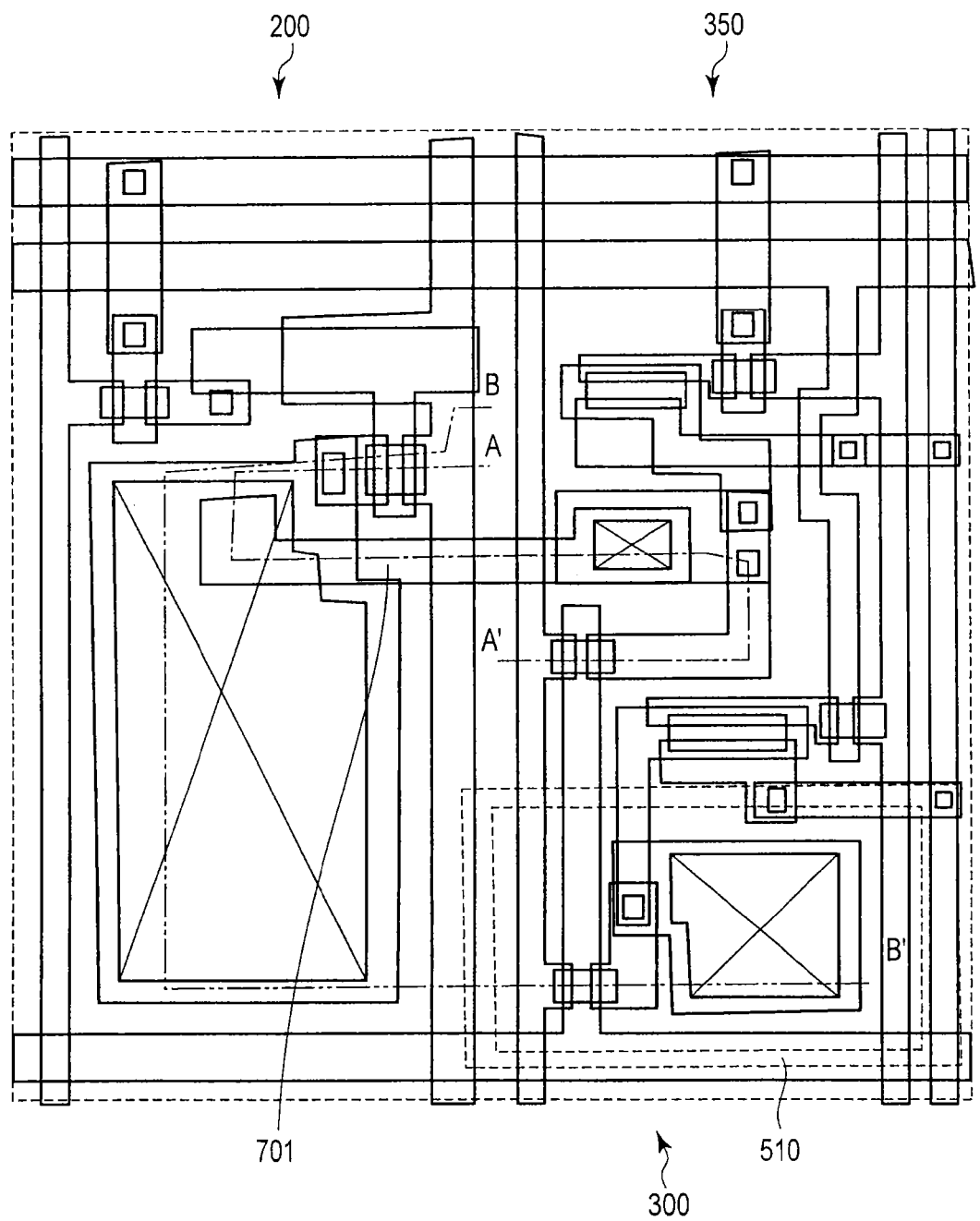
FIG. 27 is a view showing a planar layout of the pixel unit in the photoelectric conversion device shown in FIG. 26.
Figures 29A, 29B:
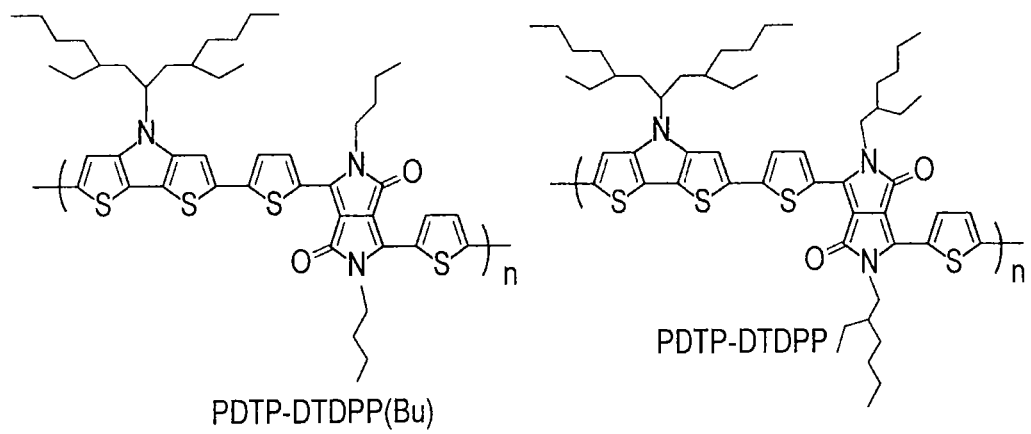
FIGS. 29A to 29D are views showing the molecular structures of semiconductor materials used in a light-receiving layer of the photoelectric conversion device of the second embodiment.
Figures 29C, 29D:
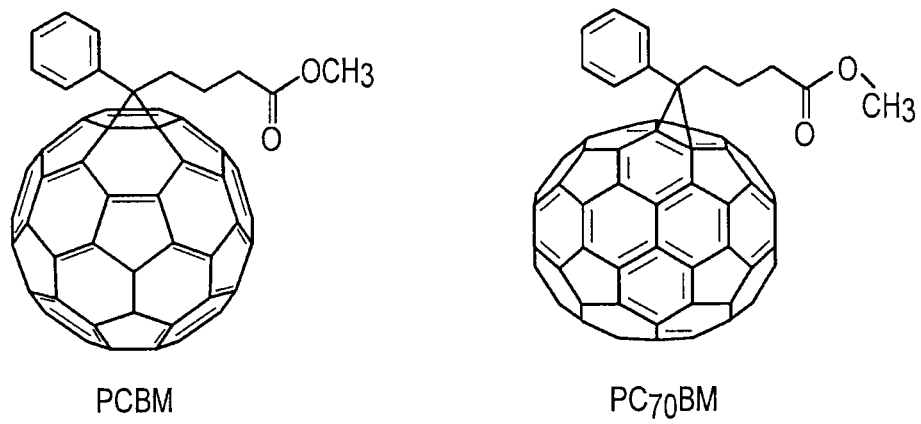

FIG. 27 shows a practical pixel layout. FIGS. 28A and 28B respectively show a section A-A' showing the optical coupling structure, and a section B-B' showing the basic structure of the light-emitting/light-receiving element. As shown in the pixel layout, in order to guide some light rays of the light-emitting element 200 to the monitor light-receiving element 350 inside the substrate as the optical coupling structure, an opaque reflecting member 701 is laid out to extend from a portion below the light-emitting element 200 to that below the light-receiving element 350. On the portion below the light-receiving element 350, the reflecting member 701 is laid out to overlap the entire light-receiving surface, thereby suppressing the influence of light rays which emerge outside the substrate and are reflected.

In the light-emitting element 200, when the reflecting member 701 is formed on a portion of one large pixel, as shown in FIG. 27, it is desirable to evaluate deterioration of the entire light-emitting element pixel. On the other hand, as the structure of the light-emitting element 200, when a step of the reflecting member causes deterioration of the light-emitting element 200 due to a leak current or electric field concentration, pixels (banks) are laid out separately for the exterior and interior uses. Then, lower electrodes may be connected, and may be driven at the same time.

Using a gate electrode layer of an array as the reflecting member 701, the number of manufacturing processes can be reduced. Another layer for the reflecting member may be arranged as needed or members of the array may be used commonly. The optical coupling mechanism by the reflecting member will be described using the sectional view shown in FIG. 28A. Light 702 which strikes the reflecting member 701 is reflected, and reaches the light-receiving element 350 after it is reflected by a cathode electrode 407 and the like. Also, light may be transmitted inside an insulating layer of the array via interface reflection, as indicated by an optical path 703. In this case, when a reflection angle becomes less than or equal to a critical angle, light is hard to be output outside the insulating layer. Hence, a scattering structure 704 is preferably provided by forming a roughened surface on the reflecting member 701 in the vicinity of the light-receiving element. After the gate electrode is formed, the surface is roughened by locally applying etching. Alternatively, a scattering surface may be locally coated and formed on the gate electrode by printing. Furthermore, an underlying insulating layer may be roughened to form an electrode above that layer.

In this manner, by arranging the optical coupling inside the substrate, the state (emission intensity deterioration or the like) of the light-emitting element 200 can be recognized independently of an external state. An amount of light brought by this coupling is preferably close to the intensity of external reflected light. When too large a light amount enters, deterioration of the light-receiving element 350 appears as a difference from the actual light-receiving element 300, thus causing a correction precision drop. It is important to assure a constant coupling amount, and it is preferable to use reflection of the reflecting member 701 and the cathode electrode 407 formed on the entire substrate.

On the other hand, as for a regular light-receiving route via the exterior, a trench 500 is formed between the light-emitting element 200 and light-receiving element 300, as shown in FIG. 28B. With this structure, reflected stray light inside the substrate can be intercepted, and only external light enters the light-receiving element 300. Thus, even when reflected light from the interior of a living body has a low intensity, it can be detected with high precision.

Modification

Note that the present invention is not limited to the aforementioned embodiments.

The structures, materials, and the like of the light-emitting element and light-receiving element are not limited to the above embodiments, and can be changed as needed depending on specifications. The material of the light-emitting layer of the light-emitting element need only be different from that of the light-receiving layer of the light-receiving element, and the upper electrodes of the light-emitting element and light-receiving element need only be commonly formed.

Also, the shape of the trench formed in the bank, the material to be buried, and the like can be changed as needed depending on specifications. Furthermore, the trench position need only be set between the light-emitting element and light-receiving element, and the material to be buried need only absorb light from the light-emitting layer.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A sensor comprising:
    light-emitting elements respectively formed in some of a plurality of pixel regions on a substrate, the light-emitting elements irradiating an interior of a living body with light;
    light-receiving elements respectively formed in some of remaining pixels of the plurality of pixel regions, the light-receiving elements each comprising:
        a sensor light-receiving element receiving the light emitted from the light-emitting element and reflected from the interior of the living body; and
        a monitor light-receiving element directly measuring some of the light emitted from the light-emitting element without emerging the light outside the substrate;
    a light-emitting element active matrix layer for driving the light-emitting element, formed on the substrate and including a thin-film transistor and an interconnection; and
    a light-receiving element active matrix layer for driving the light-receiving element, formed on the substrate and including a thin-film transistor and an interconnection,
    the sensor being configured
        to receive the light reflected from the interior of the living body and obtained when some first light-emitting elements of the light-emitting elements are driven at a first timing by the sensor light-receiving elements surrounding the driven light-emitting elements, and
        to receive the light reflected from the interior of the living body and obtained when second light-emitting elements other than the driven first light-emitting elements are driven at a second timing different from the first timing by the sensor light-receiving elements surrounding the second light-emitting elements.

2. The sensor of claim 1, wherein the substrate is a flexible substrate.

3. The sensor of claim 1, wherein
    the light-emitting element active matrix layer includes a controlling transistor and a driving transistor and operates on the light-emitting element by the driving transistor to emit light even during a period of time when the controlling transistor is in an off-state.

4. The sensor of claim 1, further comprising a driving transistor, a controlling transistor, a light-emitting element signal line, a light-emitting element scan line, and a power supply line, wherein
    a source of the controlling transistor is connected to the light-emitting element signal line, a drain of the controlling transistor is connected to a gate of the driving transistor, a gate of the controlling transistor is connected to the light-emitting element scan line, a source of the driving transistor is connected to the power supply line, and a drain of the driving transistor is connected to an anode of the light-emitting element.

5. The sensor of claim 1, wherein the substrate is transparent, and the light-emitting element emits light to a side of the substrate and the light-receiving element receives light from the side of the substrate.

6. A living body sensor comprising:
    a substrate including opaque interconnection layers;
    an insulating film formed on the substrate, the insulating film including a plurality of openings which are separated apart in a substrate in-plane direction;
    light-emitting elements respectively formed in some of the plurality of openings, each light-emitting element including a light-emitting layer formed of a semiconductor material and an upper electrode layer;
    light-receiving elements respectively formed in some of remaining openings of the plurality of openings, each light-receiving element including a light-receiving layer formed of a semiconductor material and an upper electrode layer, a light-emitting element active matrix layer for driving the light-emitting element, formed on the substrate and including a thin-film transistor and an interconnection; and a light-receiving element active matrix layer for driving the light-receiving element, formed on the substrate and including a thin-film transistor and an interconnection, the living body sensor being configured to drive some light-emitting elements of the light-emitting elements at a first timing, to irradiate an interior of a living body with light from the driven light-emitting elements and to receive the light reflected from the interior of the living body by the light-receiving elements surrounding the driven light-emitting elements; and to drive the light-emitting elements other than the driven light-emitting elements at a second timing different from the first timing, to irradiate the interior of the living body with light from the other light-emitting elements and to receive the light reflected from the interior of the living body by the light-receiving elements surrounding the other light-emitting elements.

7. The sensor of claim 6, wherein the interior of the living body is irradiated with the light from the light-emitting element through the substrate, and the light from the interior of the living body is received by the light-receiving element through the substrate, and the semiconductor material of the light-emitting element is different from the semiconductor material of the light-receiving element, the upper electrode layer of the light-emitting element and the upper electrode layer of the light-receiving element are formed as common electrodes, and each interconnection layer is formed on a region outside a region specified by the opening and in a position separated from the openings of the insulating film by distances twice or more of distances corresponding to thicknesses of the insulating film.

* * * * *